(12) United States Patent
Curro et al.

(10) Patent No.: US 7,718,243 B2
(45) Date of Patent: *May 18, 2010

(54) TUFTED LAMINATE WEB

(75) Inventors: John Joseph Curro, Cincinnati, OH (US); Robert Haines Turner, Cincinnati, OH (US); Jody Lynn Hoying, Maineville, OH (US); Susan Nicole Lloyd, Erlanger, KY (US); John Lee Hammons, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 88 days.

This patent is subject to a terminal disclaimer.

(21) Appl. No.: 12/021,369

(22) Filed: Jan. 29, 2008

(65) Prior Publication Data

US 2008/0119807 A1  May 22, 2008

Related U.S. Application Data

(63) Continuation of application No. 10/737,430, filed on Dec. 16, 2003, now Pat. No. 7,410,683, which is a continuation-in-part of application No. 10/610,299, filed on Jun. 30, 2003, now abandoned, which is a continuation-in-part of application No. 10/324,661, filed on Dec. 20, 2002, now abandoned.

(51) Int. Cl.
*B32B 3/02* (2006.01)
*B32B 3/10* (2006.01)
*B32B 5/26* (2006.01)

(52) U.S. Cl. .......................... 428/97; 428/92; 428/132; 428/133; 428/134; 428/136; 428/138; 428/139

(58) Field of Classification Search ................ 428/132, 428/133, 134, 136, 137, 138, 139, 172, 173
See application file for complete search history.

(56) References Cited

U.S. PATENT DOCUMENTS 2,068,456 A   1/1937   Hooper
2,275,425 A   3/1942   Grabec (Continued)

FOREIGN PATENT DOCUMENTS

EP   0 509 012 B1   7/1995

(Continued)

OTHER PUBLICATIONS

Office Action for U.S. Appl. No. 12/370,850 dated Jul. 8, 2009, P&G Case 9683MC; Turner et al., filed Feb. 13, 2009.

(Continued)

*Primary Examiner*—Jenna-Leigh Johnson
(74) *Attorney, Agent, or Firm*—Andrew J. Hagerty; Gary J. Foose

(57) ABSTRACT

A laminate web comprising a first and second precursor webs, at least the first precursor web being a nonwoven web, the laminate web having a first side, the first side comprising the second precursor web and at least one discrete tuft, each of the discrete tufts having a linear orientation defining a longitudinal axis and comprising a plurality of tufted fibers being integral extensions of the first precursor web and extending through the second precursor web; and a second side, the second side comprising the first precursor web.

12 Claims, 9 Drawing Sheets

U.S. PATENT DOCUMENTS

| | | |
|---|---|---|
| 2,404,758 A | 7/1946 | Teague et al. |
| 2,633,441 A | 3/1953 | Buttress |
| 2,748,863 A | 6/1956 | Benton |
| 2,924,863 A | 2/1960 | Chavannes |
| 3,073,304 A | 1/1963 | Schaar |
| 3,081,500 A | 3/1963 | Griswold et al. |
| 3,081,512 A | 3/1963 | Griswold |
| 3,137,893 A | 6/1964 | Gelpke |
| 3,355,974 A | 12/1967 | Carmichael |
| 3,511,740 A | 5/1970 | Sanders |
| 3,542,634 A | 11/1970 | Such et al. |
| 3,566,726 A | 3/1971 | Politis |
| 3,579,763 A | 5/1971 | Sommer |
| 3,681,182 A | 8/1972 | Kalwaites |
| 3,681,183 A | 8/1972 | Kalwaites |
| 3,684,284 A | 8/1972 | Tranfield |
| 3,695,270 A | 10/1972 | Dostal |
| 3,718,059 A | 2/1973 | Clayton |
| 3,760,671 A | 9/1973 | Jenkins |
| 3,881,987 A | 5/1975 | Benz |
| 3,949,127 A | 4/1976 | Ostermeier et al. |
| 3,965,906 A | 6/1976 | Karami |
| 4,035,881 A | 7/1977 | Zocher |
| 4,042,453 A | 8/1977 | Conway |
| 4,135,021 A | 1/1979 | Patchell et al. |
| 4,276,336 A | 6/1981 | Sabee |
| 4,379,799 A | 4/1983 | Holmes |
| 4,397,644 A | 8/1983 | Matthews et al. |
| 4,465,726 A | 8/1984 | Holmes |
| 4,469,734 A | 9/1984 | Minto et al. |
| 4,588,630 A | 5/1986 | Shimalla |
| 4,741,941 A | 5/1988 | Englebert et al. |
| 4,758,297 A | 7/1988 | Calligarich |
| 4,781,962 A | 11/1988 | Zamarripa et al. |
| 4,798,604 A | 1/1989 | Carter |
| 4,820,294 A | 4/1989 | Morris |
| 4,840,829 A | 6/1989 | Suzuki et al. |
| 4,859,519 A | 8/1989 | Cabe, Jr. et al. |
| 4,886,632 A | 12/1989 | Van Iten et al. |
| 4,935,087 A | 6/1990 | Gilman |
| 4,953,270 A | 9/1990 | Gilpatrick |
| 5,019,062 A | 5/1991 | Ryan et al. |
| 5,062,418 A | 11/1991 | Dyer |
| 5,144,730 A | 9/1992 | Dilo |
| 5,165,979 A | 11/1992 | Watkins et al. |
| 5,171,238 A | 12/1992 | Kajander |
| 5,180,620 A | 1/1993 | Mende |
| 5,188,625 A | 2/1993 | Van Iten et al. |
| 5,223,319 A | 6/1993 | Cotton et al. |
| 5,242,632 A | 9/1993 | Mende |
| 5,382,245 A | 1/1995 | Thompson |
| 5,383,870 A | 1/1995 | Takai et al. |
| 5,387,209 A | 2/1995 | Yamamoto et al. |
| 5,414,914 A | 5/1995 | Suzuki et al. |
| 5,415,640 A | 5/1995 | Kirby et al. |
| 5,429,854 A | 7/1995 | Currie et al. |
| 5,437,653 A | 8/1995 | Gilman et al. |
| 5,470,326 A | 11/1995 | Dabi et al. |
| 5,508,080 A | 4/1996 | Sorimachi et al. |
| 5,518,801 A | 5/1996 | Chappell et al. |
| 5,533,991 A | 7/1996 | Kirby et al. |
| 5,554,145 A | 9/1996 | Roe |
| 5,560,794 A | 10/1996 | Currie et al. |
| 5,567,501 A | 10/1996 | Srinivasan et al. |
| D375,844 S | 11/1996 | Edwards et al. |
| 5,573,719 A | 11/1996 | Fitting |
| 5,575,874 A | 11/1996 | Griesbach, III et al. |
| 5,580,418 A | 12/1996 | Alikhan |
| 5,599,420 A | 2/1997 | Yeo et al. |
| 5,624,427 A | 4/1997 | Bergman et al. |
| 5,626,571 A | 5/1997 | Young et al. |
| 5,628,097 A | 5/1997 | Benson et al. |
| 5,648,142 A | 7/1997 | Phillips |
| 5,656,119 A | 8/1997 | Srinivasan et al. |
| 5,658,639 A | 8/1997 | Curro et al. |
| 5,667,619 A | 9/1997 | Alikhan |
| 5,667,625 A | 9/1997 | Alikhan |
| 5,691,035 A | 11/1997 | Chappell et al. |
| 5,700,255 A | 12/1997 | Curro |
| 5,704,101 A | 1/1998 | Majors et al. |
| 5,709,829 A | 1/1998 | Giacometti |
| 5,714,107 A | 2/1998 | Levy et al. |
| 5,723,087 A | 3/1998 | Chappell et al. |
| 5,743,776 A | 4/1998 | Igaue |
| 5,804,021 A | 9/1998 | Abuto et al. |
| 5,814,389 A | 9/1998 | Giacometti |
| 5,817,394 A | 10/1998 | Alikhan et al. |
| 5,841,107 A | 11/1998 | Riva |
| 5,858,504 A | 1/1999 | Fitting |
| 5,879,494 A | 3/1999 | Hoff et al. |
| 5,891,544 A | 4/1999 | Chappell et al. |
| 5,895,623 A | 4/1999 | Trokhan et al. |
| 5,914,084 A | 6/1999 | Benson et al. |
| 5,916,661 A | 6/1999 | Benson et al. |
| 5,919,177 A | 7/1999 | Georger et al. |
| 5,925,026 A | 7/1999 | Arteman et al. |
| 5,964,742 A | 10/1999 | McCormack et al. |
| 5,968,029 A | 10/1999 | Chappell |
| 5,986,167 A | 11/1999 | Arteman et al. |
| 5,993,432 A | 11/1999 | Lodge et al. |
| 6,007,468 A | 12/1999 | Giacometti |
| 6,025,050 A | 2/2000 | Srinivasan et al. |
| 6,027,483 A | 2/2000 | Chappell et al. |
| 6,039,555 A | 3/2000 | Tsuji et al. |
| 6,096,016 A | 8/2000 | Tsuji et al. |
| 6,114,263 A | 9/2000 | Benson et al. |
| 6,117,524 A | 9/2000 | Hisanaka et al. |
| 6,120,718 A | 9/2000 | Kotek et al. |
| 6,129,801 A | 10/2000 | Benson et al. |
| 6,155,083 A | 12/2000 | Goeser et al. |
| 6,168,849 B1 | 1/2001 | Braverman et al. |
| 6,176,954 B1 | 1/2001 | Tsuji et al. |
| 6,247,914 B1 | 6/2001 | Lindquist et al. |
| D444,631 S | 7/2001 | Woodbridge et al. |
| 6,264,872 B1 | 7/2001 | Majors et al. |
| 6,287,407 B1 | 9/2001 | Stein et al. |
| 6,383,431 B1 | 5/2002 | Dobrin et al. |
| 6,395,211 B1 | 5/2002 | Dettmer et al. |
| 6,410,823 B1 | 6/2002 | Daley et al. |
| 6,420,625 B1 | 7/2002 | Jones et al. |
| 6,423,884 B1 | 7/2002 | Oehmen |
| 6,451,718 B1 | 9/2002 | Yamada et al. |
| 6,452,064 B1 | 9/2002 | Thoren et al. |
| 6,458,447 B1 | 10/2002 | Cabell |
| D466,702 S | 12/2002 | Carlson et al. |
| 6,506,329 B1 | 1/2003 | Curro et al. |
| 6,537,936 B1 | 3/2003 | Busam et al. |
| 6,620,485 B1 | 9/2003 | Benson et al. |
| 6,632,504 B1 | 10/2003 | Gillespie et al. |
| D481,872 S | 11/2003 | Hennel et al. |
| 6,669,878 B2 | 12/2003 | Konishi et al. |
| 6,716,498 B2 | 4/2004 | Curro et al. |
| 6,726,870 B1 | 4/2004 | Benson et al. |
| 6,736,916 B2 | 5/2004 | Steinke et al. |
| 6,794,626 B2 | 9/2004 | Kiermeier et al. |
| 6,808,791 B2 | 10/2004 | Curro et al. |
| 6,818,802 B2 | 11/2004 | Takai et al. |
| 6,830,800 B2 | 12/2004 | Curro et al. |
| 6,837,956 B2 | 1/2005 | Cowell et al. |
| 6,863,960 B2 | 3/2005 | Curro et al. |
| 6,872,274 B2 | 3/2005 | Kauschke et al. |
| 6,884,494 B1 | 4/2005 | Curro et al. |
| 7,005,558 B1 | 2/2006 | Johansson et al. |
| 7,037,569 B2 | 5/2006 | Curro et al. |

| | | | |
|---|---|---|---|
| 2002/0029445 | A1 | 3/2002 | Stein et al. |
| 2002/0039867 | A1 | 4/2002 | Curro et al. |
| 2002/0103469 | A1 | 8/2002 | Chen et al. |
| 2002/0105110 | A1 | 8/2002 | Dobrin et al. |
| 2002/0107495 | A1 | 8/2002 | Chen et al. |
| 2002/0119720 | A1 | 8/2002 | Arora et al. |
| 2002/0132544 | A1 | 9/2002 | Takagaki |
| 2003/0021951 | A1 | 1/2003 | Desai et al. |
| 2003/0085213 | A1 | 5/2003 | Burckhardt et al. |
| 2003/0191442 | A1 | 10/2003 | Bewick-Sonntag |
| 2003/0191443 | A1 | 10/2003 | Taylor |
| 2004/0022993 | A1 | 2/2004 | Wildeman |
| 2004/0121686 | A1 | 6/2004 | Wong et al. |
| 2004/0122396 | A1 | 6/2004 | Maldonado et al. |
| 2004/0126531 | A1 | 7/2004 | Harvey et al. |
| 2004/0131820 | A1 | 7/2004 | Turner et al. |
| 2004/0137200 | A1 | 7/2004 | Chhabra et al. |
| 2004/0157036 | A1 | 8/2004 | Provost et al. |
| 2004/0229008 | A1 | 11/2004 | Hoying et al. |
| 2004/0242097 | A1 | 12/2004 | Hasenoehrl et al. |
| 2004/0265533 | A1 | 12/2004 | Hoying et al. |
| 2004/0265534 | A1 | 12/2004 | Curro et al. |
| 2005/0064136 | A1 | 3/2005 | Turner et al. |
| 2005/0096614 | A1 | 5/2005 | Perez et al. |
| 2005/0123726 | A1 | 6/2005 | Broering et al. |
| 2005/0283129 | A1 | 12/2005 | Hammons et al. |
| 2006/0019056 | A1 | 1/2006 | Turner et al. |
| 2006/0087053 | A1 | 4/2006 | O'Donnell et al. |
| 2006/0286343 | A1 | 12/2006 | Curro et al. |

FOREIGN PATENT DOCUMENTS

| | | | |
|---|---|---|---|
| EP | 0 955 159 | A1 | 11/1999 |
| EP | 0 963 747 | A1 | 12/1999 |
| EP | 1 004 412 | A1 | 5/2000 |
| FR | 2 713 083 | A1 | 6/1995 |
| WO | WO 95/15138 | | 6/1995 |
| WO | WO 01/45616 | A1 | 6/2001 |
| WO | WO 01/76523 | A2 | 10/2001 |
| WO | WO 02/100632 | A1 | 12/2002 |
| WO | WO 2005/011936 | A1 | 2/2005 |

OTHER PUBLICATIONS

Office Action for U.S. Appl. No. 11/158,165 dated May 16, 2008; P&G Case 9683M; Turner et al., filed Jun. 21, 2005.
Office Action for U.S. Appl. No. 11/158,165 dated Dec. 7, 2007; P&G Case 9683M; Turner et al.; filed Jun. 21, 2005.
Office Action for U.S. Appl. No. 11/158,165 dated Jul. 3, 2007; P&G Case 9683M; Turner et al, filed Jun. 21, 2005.
Office Action for U.S. Appl. No. 11/157,770 dated Apr. 28, 2009; P&G Case 9682M; Hammons et al., filed Jun. 21, 2005.
Office Action for U.S. Appl. No. 11/157,770 dated Jun. 2, 2008; P&G Case 9682M; Hammons et al., filed Jun. 21, 2005.
Office Action for U.S. Appl. No. 11/157,770 dated Oct. 1, 2007; P&G Case 9682M; Hammons et al., filed Jun. 21, 2005.
Office Action for U.S. Appl. No. 11/156,020 dated Jul. 8, 2009; P&G Case 9681M; Curro et al., filed Jun. 17, 2005.
Office Action for U.S. Appl. No. 11/156,020 dated Dec. 24, 2008; P&G Case 9681M; Curro et al., filed Jun. 17, 2005.
Office Action for U.S. Appl. No. 11/156,020 dated Jul. 10, 2008; P&G Case 9681M; Curro et al., filed Jun. 17, 2005.
Office Action for U.S. Appl. No. 11/156,020 dated Nov. 27, 2007; P&G Case 9681M; Curro et al., filed Jun. 17, 2005.
Office Action for U.S. Appl. No. 11/156,020 dated Jun. 20, 2007; P&G Case 9681M; Curro et al.; filed Jun. 17, 2005.
Office Action for U.S. Appl. No. 11/156,020 dated Jan. 2, 2007; P&G Case 9681M; Curro et al., filed Jun. 17, 2005.
Examiner's Answer for U.S. Appl. No. 11/155,805 dated Aug. 6, 2009 P&G Case 9680M; Curro et al., filed Jun. 17, 2005.
Office Action for U.S. Appl. No. 11/155,805 dated Oct. 30, 2008; P&G Case 9680M; Curro et al., filed Jun. 17, 2005.
Office Action for U.S. Appl. No. 11/155,805 dated May 16, 2008; P&G Case 9680M; Curro et al., filed Jun. 17, 2005.
Office Action for U.S. Appl. No. 11/155,805 dated Nov. 27, 2007; P&G Case 9680M; Curro et al., filed Jun. 17, 2005.
Office Action for U.S. Appl. No. 11/155,805 dated Jun. 19, 2007; P&G Case 9680M; Curro et al., filed Jun. 17, 2005.
Office Action for U.S. Appl. No. 10/737,235 dated May 6, 2009; P&G Case 9456; Hoying et al., filed Dec. 16, 2003.
Office Action for U.S. Appl. No. 10/737,235 dated Nov. 25, 2008; P&G Case 9456; Hoying et al., filed Dec. 16, 2003.
Office Action for U.S. Appl. No. 10/737,235 dated Jun. 12, 2008; P&G Case 9456; Hoying et al., filed Dec. 16, 2003.
Office Action for U.S. Appl. No. 10/737,235 dated Dec. 12, 2007; P&G Case 9456; Hoying et al., filed Dec. 16, 2003.
Office Action for U.S. Appl. No. 10/737,235 dated Jul. 26, 2007; P&G Case 9456; Hoying et al., filed Dec. 16, 2003.
Office Action for U.S. Appl. No. 10/737,235 dated Feb. 6, 2007; P&G Case 9456; Hoying et al., filed Dec. 16, 2003.
Office Action for U.S. Appl. No. 10/737,235 dated Aug. 8, 2006; P&G Case 9456; Hoying et al., filed Dec. 16, 2003.
Office Action for U.S. Appl. No. 10/737,235 dated Feb. 3, 2006; P&G Case 9456; Hoying et al., filed Dec. 16, 2003.
Office Action for U.S. Appl. No. 10/737,235 dated Aug. 24, 2005; P&G Case 9456; Hoying et al., filed Dec. 16, 2003.
Office Action for U.S. Appl. No. 11/650,821 dated Mar. 16, 2009; P&G Case 9455C; Hoying et al., filed Jan. 8, 2007.
Office Action for U.S. Appl. No. 11/650,821 dated Oct. 8, 2008; P&G Case 9455C; Hoying et al., filed Jan. 8, 2007.
Office Action for U.S. Appl. No. 11/650,821 dated Apr. 23, 2008; P&G Case 9455C; Hoying et al., filed Jan. 8, 2007.
Office Action for U.S. Appl. No. 11/650,821 dated Oct. 16, 2007; P&G Case 9455C; Hoying et al., filed Jan. 8, 2007.
Notice of Allowance for U.S. Appl. No. 10/737,307 dated Sep. 28, 2006; P&G Case 9455; Hoying et al., filed Dec. 16, 2003.
Office Action for U.S. Appl. No. 10/737,307 dated May 31, 2006; P&G Case 9455; Hoying et al., filed Dec. 16, 2003.
Office Action for U.S. Appl. No. 10/737,307 dated Oct. 7, 2005; P&G Case 9455; Hoying et al., filed Dec. 16, 2003.
Notice of Allowance for U.S. Appl. No. 10/980,219 dated May 23, 2007; P&G Case 9313RR; Broering et al., filed Nov. 3, 2004.
Office Action for U.S. Appl. No. 10/980,219 dated Mar. 5, 2007; P&G Case 9313RR; Broering et al., filed Nov. 3, 2004.
Office Action for U.S. Appl. No. 10/980,219 dated Sep. 11, 2006; P&G Case 9313RR; Broering et al., filed Nov. 3, 2004.
Notice of Allowance for U.S. Appl. No. 10/737,430 dated Mar. 18, 2008; P&G Case 9313R; Curro et al., filed Dec. 16, 2003.
Notice of Allowance for U.S. Appl. No. 10/737,430 dated Oct. 29, 2007; P&G Case 9313R; Curro et al., filed Dec. 16, 2003.
Office Action for U.S. Appl. No. 10/737,430 dated Jul. 16, 2007; P&G Case 9313R; Curro et al., filed Dec. 16, 2003.
Office Action for U.S. Appl. No. 10/737,430 dated Jan. 25, 2007; P&G Case 9313R; Curro et al., filed Dec. 16, 2003.
Office Action for U.S. Appl. No. 10/737,430 dated Aug. 8, 2006; P&G Case 9313R; Curro et al., filed Dec. 16, 2003.
Office Action for U.S. Appl. No. 10/737,430 dated Feb. 3, 2006; P&G Case 9313R; Curro et al., filed Dec. 16, 2003.
Office Action for U.S. Appl. No. 10/737,430 dated Aug. 24, 2005; P&G Case 9313R; Curro et al., filed Dec. 16, 2003.
Office Action for U.S. Appl. No. 10/737,306 dated Jun. 12, 2008; P&G Case 9134R2; Gray et al., filed Mar. 28, 2003.
Notice of Allowance for U.S. Appl. No. 10/737,306 dated Nov. 29, 2007; P&G Case 9134R2; Gray et al., filed Mar. 28, 2003.
Office Action for U.S. Appl. No. 10/737,306 dated Jul. 16, 2007; P&G Case 9134R2; Gray et al., filed Mar. 28, 2003.
Office Action for U.S. Appl. No. 10/737,306 dated Jan. 26, 2007; P&G Case 9134R2; Gray et al., filed Mar. 28, 2003.
Office Action for U.S. Appl. No. 10/737,306 dated Aug. 9, 2006; P&G Case 9134R2; Gray et al., filed Mar. 28, 2003.
Office Action for U.S. Appl. No. 10/737,306 dated Aug. 24, 2005; P&G Case 9134R2; Gray et al., filed Mar. 28, 2003.
Office Action for U.S. Appl. No. 10/737,306 dated Feb. 3, 2006; P&G Case 9134R2; Gray et al., filed Mar. 28, 2003.

Office Action for U.S. Appl. No. 11/129,877 dated Mar. 30, 2007; P&G Case 9684M; Cabell, filed May 16, 2005.

Office Action for U.S. Appl. No. 11/129,877 dated Oct. 2, 2007; P&G Case 9684M; Cabel, filed May 16, 2005.

Office Action for U.S. Appl. No. 11/129,877 dated Jan. 23, 2008; P&G Case 9684M; Cabell, filed May 16, 2005.

Office Action for U.S. Appl. No. 11/129,877 dated Jun. 12, 2008; P&G Case 9684M; Cabell, filed May 16, 2005.

TUFTED LAMINATE WEB

CROSS-REFERENCE TO RELATED APPLICATION

This application is a continuation of U.S. patent application Ser. No. 10/737,430, filed Dec. 16, 2003, now U.S. Pat. No. 7,410,683, which is a continuation-in-part of U.S. patent application Ser. No. 10/6 10,299, filed Jun. 30, 2003, now abandoned, which is a continuation-in-part of U.S. patent application Ser. No. 10,324,661, filed Dec. 20, 2002, now abandoned.

FIELD OF INVENTION

This invention relates to webs such as films and fibrous woven and nonwoven webs. In particular, this invention relates to laminates of such webs treated by mechanical formation to have increased softness or bulk properties.

BACKGROUND OF THE INVENTION

Laminates of webs, such as films and fibrous webs are well known in the art. For example, nonwoven webs are often laminated with polymer films such that they are useful as materials in disposable products such as backsheets on disposable absorbent diapers, for example. In such laminates the nonwoven portion can provide softness while the film portion can provide for fluid impermeability.

In many applications it is desirable that laminates of webs have a bulky texture and/or softness. Additionally, it is desirable that laminates of webs have the texture and softness different on the two sides of the web. That is, the web can have a textured, relatively rough surface on one side, and a soft, relatively smooth surface on the other side. This can be achieved by laminating two dissimilar webs together, such as by adhesive or thermal bonding means. For example, a tufted nonwoven web can be adhered by adhesive to a non-tufted nonwoven web to make a laminate web having two sides with very different textures and softness characteristics.

Additionally, it is known to combine into a laminate two nonwoven materials to gain the benefits of dissimilar materials in a single laminate web. For example, it is known to needlepunch nonwoven webs to produce integrally-bonded and entangled nonwoven webs. This process is often simply referred to as "needling." U.S. Pat. No. 5,080,951 granted Jan. 14, 1992 to Guthrie, for example, discloses a nonwoven web composed of multiple layers bonded by a needling process that causes some fibers to extend through the entire thickness of the fabric and beyond the surface, thereby leaving short segments of filaments protruding from the exterior surface of the web. Frequently hydroentangling is used to accomplish a similar entangling of two fibrous nonwoven webs. Needling, like fluid entangling, is a relatively slow and therefore expensive process for manufacture of nonwoven webs, particularly for webs intended for disposable article use.

In general, current methods for making laminates of films and fibrous webs having bulky or tufted textures on at least one side thereof are either relatively expensive for many applications of such webs, or the resulting webs are too stiff due to the application of adhesives or thermal bonding.

Accordingly, there is a need for a low cost laminate web having terry cloth-like properties.

Additionally, there is a need for a laminate web in which a nonwoven having tufted regions and a film or another nonwoven layer can be joined, preferably by means that do not require adhesives or thermal bonding to remain laminated.

Additionally, there is a need for a laminate web in which the layers are not only joined to but also integrated through one another.

Additionally, there is a need for a method of relatively inexpensively making a laminate web having terry cloth-like properties.

Further, there is a need for a low cost method of making a soft, high bulk porous laminate web of film, woven and/or nonwoven material.

SUMMARY OF THE INVENTION

A laminate web comprising a first and second precursor webs, at least the first precursor web being a nonwoven web, the laminate web having a first side, the first side comprising the second precursor web and at least one discrete tuft, each of the discrete tufts having a linear orientation defining a longitudinal axis and comprising a plurality of tufted fibers being integral extensions of the first precursor web and extending through the second precursor web; and a second side, the second side comprising the first precursor web.

DETAILED DESCRIPTION OF THE INVENTION

Figure 1:
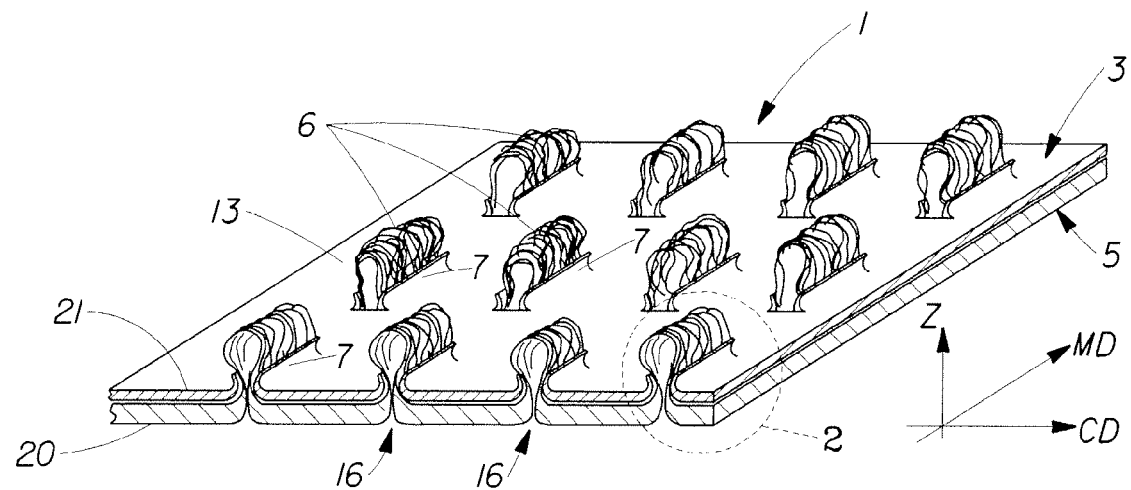
FIG. 1 is a perspective view of a web of the present invention.

FIG. 1 shows a laminate web 1 of the present invention, hereinafter referred to simply as web 1. Web 1 comprises at least two layers. The layers are referred to herein as generally planar, two-dimensional precursor webs, such as first precursor web 20 and second precursor web 21. Either precursor web can be a film, a nonwoven, or a woven web. Precursor webs 20 and 21 (and any additional webs) can be joined by adhesive, thermal bonding, ultrasonic bonding and the like, but are preferably joined without the use of adhesive or other forms of bonding. As disclosed below, the constituent precursor webs of web 1 can be joined by interlocking mechanical engagement resulting from the formation of tufts 6.

Web 1 has a first side 3 and a second side 5, the term "sides" being used in the common usage of generally planar two-dimensional webs, such as paper and films that have two sides when in a generally flat condition. Each precursor web 20 and 21 has a first surface 12 and 13, respectively, and a second surface 14 and 15, respectively (shown in FIG. 3). Web 1 has a machine direction (MD) and a cross machine direction (CD) as is commonly known in the art of web manufacture. Although the present invention can be practiced with polymer films and woven webs, in a preferred embodiment first precursor web 20 is a nonwoven web comprised of substantially randomly oriented fibers. By "substantially randomly oriented" is meant that, due to processing conditions of the precursor web, there may be a higher amount of fibers oriented in the MD than the CD, or vice-versa. For example, in spunbonding and meltblowing processes continuous strands of fibers are deposited on a support moving in the MD. Despite attempts to make the orientation of the fibers of the spunbond or meltblown nonwoven web truly "random," usually a slightly higher percentage of fibers are oriented in the MD as opposed to the CD. In a preferred embodiment, second precursor web 21 is a nonwoven web similar to the first precursor web 20, or a polymer film or an apertured polymer film, such as a polyethylene film.

Figure 3:
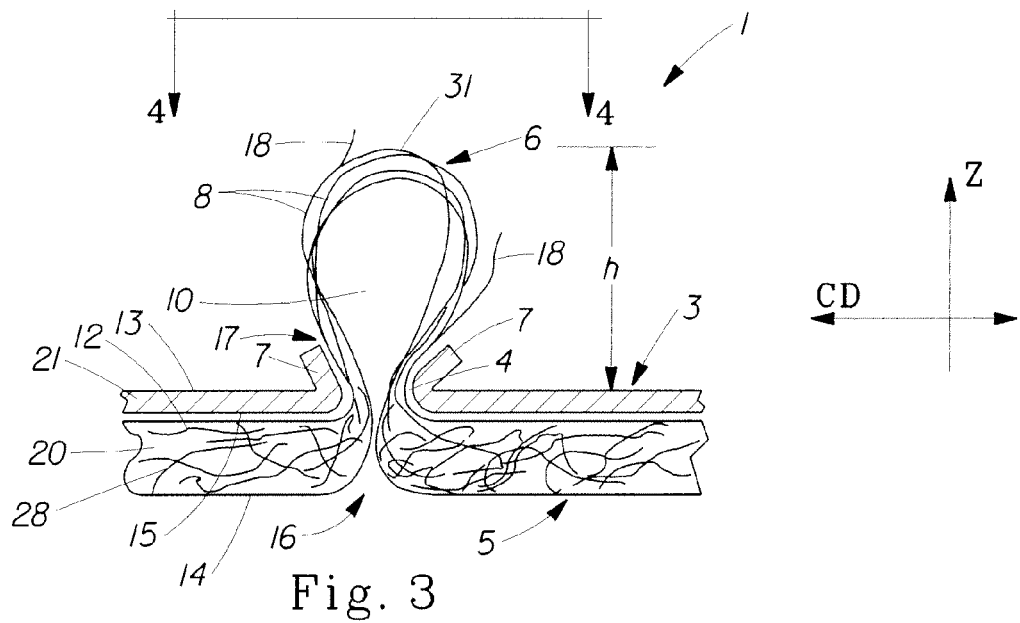
FIG. 3 is a cross-sectional view of section 3-3 of FIG. 2.

In one embodiment, first side 3 of web 1 is defined by exposed portions of the first surface 13 of second precursor web 21 and at least one, but preferably a plurality of, discrete tufts 6 which are integral extensions of the fibers of a nonwoven first precursor web 20. As shown in FIG. 3, each tuft 6 can comprise a plurality of looped, aligned fibers 8 extending through second precursor web 21 and outwardly from the first surface 13 thereof. In another embodiment each tuft 6 can comprise a plurality of non-looped fibers 18 (as shown in FIG. 3) that extend outwardly from the first surface 13.

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, meltblowing processes, spunbonding processes, hydroentangling, airlaying, and bonded carded web processes, including carded thermal bonding. The basis weight of nonwoven fabrics is usually expressed in grams per square meter (gsm). The basis weight of the laminate web is the combined basis weight of the constituent layers and any other added components. Fiber diameters are usually expressed in microns; fiber size can also be expressed in denier, which is a unit of weight per length of fiber. The basis weight of laminate webs suitable for use in the present invention can range from 10 gsm to 500 gsm, depending on the ultimate use of the web 1. For use as a hand towel, for example, both first precursor web 20 and second precursor web 21 can be a nonwoven web having a basis weight for of between 25 gsm and 100 gsm. For use as a bath towel both first precursor web 20 and second precursor web 21 can have a basis weight for of between 125 gsm and 250 gsm. For use as a ground cover, such an erosion control liners, a laminate basis weight of between 350 gsm and 500 gsm or higher may be appropriate.

The constituent fibers of nonwoven precursor web 20 or 21 can be comprised of polymers such as polyethylene, polypropylene, polyester, and blends thereof. The fibers can comprise cellulose, rayon, cotton, or other natural materials or blends of polymer and natural materials. The fibers can also comprise a super absorbent material such as polyacrylate or any combination of suitable materials. The fibers can be monocomponent, bicomponent, and/or biconstituent, non-round (e.g., capillary channel fibers), and can have major cross-sectional dimensions (e.g., diameter for round fibers) ranging from 0.1-500 microns. For example, one type of fibers suitable for the nonwoven web includes nanofibers. Nanofibers are described as fibers having a mean diameter of less than 1 micron. Nanofibers can comprise all of the fibers in a nonwoven web or a portion of the fibers in a nonwoven web. The constituent fibers of the nonwoven precursor web may also be a mixture of different fiber types, differing in such features as chemistry (e.g. PE and PP), components (mono- and bi-), denier (micro denier and >20 denier), shape (i.e. capillary and round) and the like. The constituent fibers can range from about 0.1 denier to about 100 denier.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky, to form a web of randomly dispersed meltblown fibers. Meltblown fibers are microfibers which may be continuous or discontinuous and are generally smaller than 10 microns in average diameter.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multi-constituent fibers.

As used herein, the term "non-round fibers" describes fibers having a non-round cross-section, and includes "shaped fibers" and "capillary channel fibers." Such fibers can be solid or hollow, and they can be tri-lobal, delta-shaped, and are preferably fibers having capillary channels on their outer surfaces. The capillary channels can be of various cross-sectional shapes such as "U-shaped", "H-shaped", "C-shaped" and "V-shaped". One preferred capillary channel fiber is T-401, designated as 4DG fiber available from Fiber Innovation Technologies, Johnson City, Tenn. T-401 fiber is a polyethylene terephthalate (PET polyester).

As used herein, the term "integral" as in "integral extension" when used for the tufts 6 refers to fibers of the tufts 6 having originated from the fibers of the first precursor web 20. Therefore, the looped fibers 8 and non-looped fibers 18 of tufts 6, can be plastically deformed and extended fibers of the first precursor web 20, and are, therefore, integral with first precursor web 20. As used herein, "integral" is to be distinguished from fibers introduced to or added to a separate precursor web for the purpose of making tufts, as is commonly done in conventional carpet making, for example.

The number, spacing, and dimensions of tufts 6 can be varied to give varying texture to first side 3 of web 1. For example, if tufts 6 are sufficiently closely spaced the first side 3 of web 1 can have a terry cloth-like feel. Alternatively, tufts 6 can be arranged in patterns such as lines or filled shapes to create portions of a laminate web having greater texture, softness, bulk, absorbency or visual design appeal. For example, when tufts 6 are arranged in a pattern of a line or lines, the tufts can have the appearance of stitching. Tufts 6 can also be arranged to form specific shapes, such as designs, words or logos. Such shapes can be used, for example, on laminates useful for hotel bath towels or robes which can have the name or logo of the hotel formed thereon. Likewise, the size dimensions, such as the height, length and width of individual tufts 6 can be varied. Single tufts can be as long as about 3 cm in length and can be made alone or dispersed among tufts of various sizes.

First precursor web 20 can be a fibrous woven or nonwoven web comprising fibers having sufficient elongation properties to have portions formed into tufts 6 as described more fully below. Tufts are formed by urging fibers out-of-plane in the Z-direction at discrete, localized, portions of first precursor web 20. The urging out-of-plane can be due to fiber displacement, i.e., the fiber is able to move relative to other fibers and be "pulled," so to speak, out-of-plane. More often, however, for most nonwoven first precursor webs 20, the urging out-of-plane is due to the fibers of tufts 6 having been at least partially plastically stretched and permanently deformed to form tufts 6. Therefore, in one embodiment, depending on the desired height of tufts 6, the constituent fibers of a nonwoven first precursor webs 20 can exhibit an elongation to break of at least about 5%, more preferably at least about 10%, more preferably at least about 25%, more preferably at least about 50%, and more preferably at least about 100%. Elongation to break can be determined by simple tensile testing, such as by use of Instron tensile testing equipment, and can generally be found on material data sheets from suppliers of such fibers or webs.

It can be appreciated that a suitable nonwoven first precursor web 20 should comprise fibers capable of experiencing sufficient plastic deformation and tensile elongation, or are capable of sufficient fiber mobility, such that looped fibers 8 are formed. However, it is recognized that a certain percentage of fibers urged out of the plane of the first surface 12 of first precursor web 20 will not form a loop, but instead will break and form loose ends. Such fibers are referred to herein as "loose" fibers or "loose fiber ends" 18 as shown in FIG. 3. Loose fiber ends 18 are not necessarily undesirable for the present invention, and in some embodiments, most or all of the fibers of tufts 6 can be loose fiber ends 18. Loose fiber ends 18 can also be the result of forming tufts 6 from nonwoven webs consisting of, or containing, cut staple fibers. In such a case, some number of the staple fiber ends may protrude into the tuft 6, depending upon such things as the number of staple fibers in the web, the staple fiber cut length, and the height of the tufts. In some instances, it may be desired to use a blend of fibers of different lengths in a precursor web or fibers of different lengths in different layers. This may be able to selectively separate the longer fibers from the shorter fibers. The longer fibers may predominately form the tuft 6 while the shorter fibers predominately remain in the portion of the web not forming the tuft 6. An exemplary mixture of fiber lengths can include fibers of approximately 2 to 8 centimeters for the longer fibers and less than about 1 centimeter for the shorter fibers.

First precursor web 20 can be a fibrous woven or nonwoven web comprising elastic or elastomeric fibers. Elastic or elastomeric fibers can be stretched at least about 50% and return to within 10% of their original dimension. Tufts 6 can be formed from elastic fibers if the fibers are simply displaced due to the mobility of the fiber within the nonwoven, or if the fibers are stretched beyond their elastic limit and are plastically deformed.

Second precursor web 21 can be virtually any web material, the only requirement being that it have sufficient integrity to be formed into the laminate by the process described below, and that it have sufficiently less elongation properties relative to first precursor web 20, such that upon experiencing the strain of fibers from first precursor web 20 being urged out-of-plane in the direction of second precursor web 21, second precursor web 21 will rupture, e.g., by tearing due to extensional failure, such that portions of first precursor web 20 can extend through, (i.e., "punch through" so to speak), second precursor web 21 to form tufts 6 on first side 3 of web 1. In one embodiment second precursor web 21 is a polymer film. Second precursor web 21 can also be a woven textile web, a nonwoven web, a polymer film, an apertured polymer film, a paper web, (e.g., tissue paper), a metal foil (e.g., aluminum wrapping foil), a foam (e.g., urethane foam sheeting), or the like.

Figure 2:
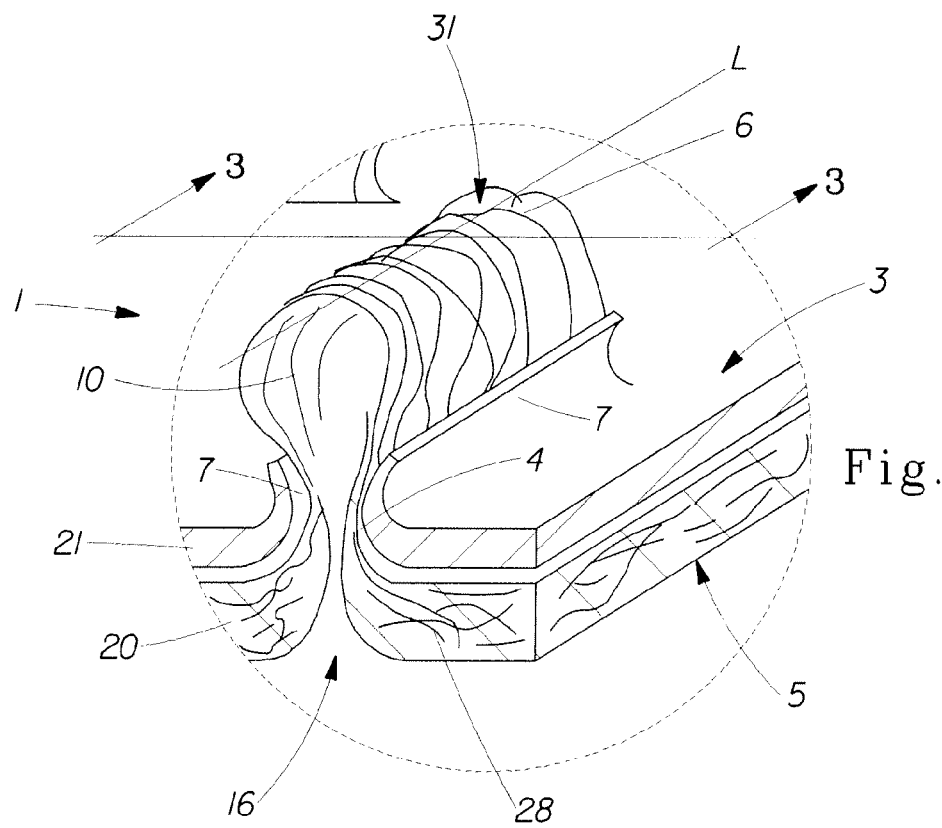
FIG. 2 is an enlarged view of a portion of the web shown in FIG. 1.

A representative tuft 6 for the embodiment of web 1 shown in FIG. 1 is shown in a further enlarged view in FIG. 2. As shown in FIG. 2 or 3, tuft 6 comprises a plurality of looped fibers 8 that are substantially aligned such that tuft 6 has a distinct linear orientation and a longitudinal axis L. Tuft 6 also have a transverse axis T generally orthogonal to longitudinal axis L in the MD-CD plane. In the embodiment shown in FIGS. 1 and 2, longitudinal axis L is parallel to the MD. In one embodiment, all the spaced apart tufts 6 have generally parallel longitudinal axes L. The number of tufts 6 per unit area of web 1, i.e., the area density of tuft 6, can be varied from 1 tuft per unit area, e.g., square centimeter to as high as 100 tufts per square centimeter. There can be at least 10, or at least 20 tufts 6 per square centimeter, depending on the end use. In general, the area density need not be uniform across the entire area of web 1, but tufts 6 can be only in certain regions of web 1, such as in regions having predetermined shapes, such as lines, stripes, bands, circles, and the like.

As can be appreciated by the description herein, in many embodiments of web 1 openings 4 of second precursor web 21 will have a distinct linear orientation and a longitudinal axis, which is oriented parallel to the longitudinal axis L of its corresponding tuft 6. Likewise, openings 4 will also have a transverse axis generally orthogonal to longitudinal axis in the MD-CD plane.

As shown in FIGS. 1-4, tufts 6 extend through openings 4 in second precursor web 21. Openings 4 are formed by locally rupturing second precursor web 21 by the process described in detail below. Rupture may involve a simple splitting open of second precursor web 21, such that opening 4 remains a simple two-dimensional aperture. However, for some materials, such as polymer films, portions of second precursor web 21 can be deflected or urged out-of-plane (i.e., the plane of second precursor web 21) to form flap-like structures, referred to herein as flap, or flaps, 7. The form and structure of flaps 7 is highly dependent upon the material properties of second precursor web 21. Flaps 7 can have the general structure of one or more flaps, as shown in FIGS. 1 and 2. In other embodiments, flap 7 can have a more volcano-like structure, as if the tuft 6 is erupting from the flap 7.

In one embodiment flaps 7 do not contribute significantly to the material of tufts 6, and particularly do not contribute significantly to the tactile quality of tufts 6. In one embodiment, therefore, the laminate web 1 comprises at least two layers (i.e., precursor webs 20 and 21), but at least one of the layers (i.e., precursor web 21 in FIGS. 1-4) does not significantly affect on the tactile qualities of tufts 6.

In one embodiment, flaps 7 may extend out of plane significantly, even being as high, so to speak, as the tufts 6 themselves. In this embodiment flaps 7 can cause the tufts 6 to be more resilient and less susceptible to flattening due to compressive or bending forces. In one embodiment, therefore, the laminate web 1 comprises at least two layers (i.e., precursor webs 20 and 21), and both layers affect the tactile qualities of tufts 6.

Tufts 6 are, in a sense, "punched through" second precursor web 21 and can be "locked" in place by frictional engagement with openings 4. In some embodiments, for example, the lateral width of opening 4 (i.e., the dimension measured parallel to its transverse axis) can be less than the maximum width of the tooth that formed the opening (per the process described below). This indicates a certain amount of recovery at the opening that tends to constrain tuft 6 from pulling back out through opening 4. The frictional engagement of the tufts and openings provides for a laminate web structure having permanent tufting on one side that can be formed without adhesives or thermal bonding.

Because in some embodiments at least one of the layers (e.g., a relatively low elongation polymer film or tissue paper second precursor web 21 in FIGS. 1-4) does not significantly contribute material to the tufts 6 (such as in the embodiments shown in FIGS. 1-4) a web 1 comprising a nonwoven first precursor web 20 can be characterized as being predominantly fibrous on both sides of web 1 with the fibers being contributed only by nonwoven first precursor web 20. Therefore, tufts 6 can be spaced sufficiently closely so as to effectively cover first side 3 of web 1. In such an embodiment, both sides of web 1 appear to be nonwoven, with a difference between the two sides 3 and 5 being a difference in surface texture. Therefore, in one embodiment, the invention can be described as a laminate material of two or more precursor webs, wherein both sides of the laminate web are substantially covered by fibers from only one of the precursor webs.

As shown in FIGS. 1-4, one characteristic of tufts 6 can be the predominant directional alignment of the fibers 8 or 18. For example, looped, aligned fibers 8 can be described as having a significant or major vector component parallel to the Z-CD plane and the looped fibers 8 have a substantially uniform alignment with respect to transverse axis T when viewed in plan view, such as in FIG. 4. By "looped" fibers 8 is meant fibers 8 that are integral with and begin and end in first precursor web 20 but extend outwardly in the Z-direction from first surface 13 of second precursor web 21. By "aligned" with respect to looped fibers 8 of tufts 6 is meant that looped fibers 8 are all generally oriented such that, if viewed in plan view as in FIG. 4, each of the looped fibers 8 has a significant vector component parallel to the transverse axis T, and preferably a major vector component parallel to the transverse axis T.

In contrast, non-looped fibers 18 are integral with, but only begin in first precursor web 20 and have a free end extending outwardly in the Z-direction from first surface 13 of second precursor web 21. Loose fibers 18 can also have a generally uniform alignment described as having a significant or major vector component parallel to the Z-CD plane.

For both looped fibers 8 and loose fibers 18, the alignment is a characteristic of tufts 6 prior to any post-manufacture deformation due to winding onto a roll, or compression in use in an article of manufacture.

Figure 4:
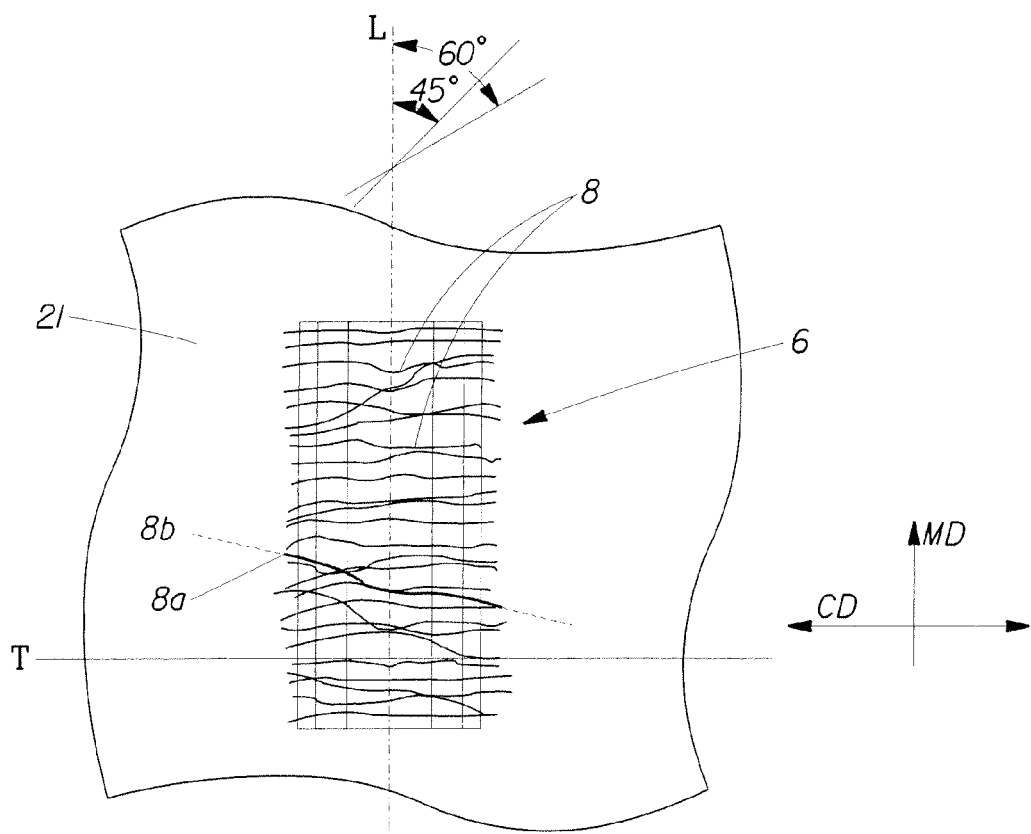
FIG. 4 is a plan view of a portion of the web as indicated by 4-4 in FIG. 3.

As used herein, a looped fiber 8 oriented at an angle of greater than 45 degrees from the longitudinal axis L when viewed in plan view, as in FIG. 4, has a significant vector component parallel to the transverse axis T. As used herein, a looped fiber 8 oriented at an angle of greater than 60 degrees from longitudinal axis L when viewed in plan view, as in FIG. 4, has a major vector component parallel to the transverse axis T. In a preferred embodiment, at least 50%, more preferably at least 70%, and more preferably at least 90% of fibers 8 of tuft 6 have a significant, and more preferably, a major vector component parallel to transverse axis T. Fiber orientation can be determined by use of magnifying means if necessary, such as a microscope fitted with a suitable measurement scale. In general, for a non-linear segment of fiber viewed in plan view, a straight-line approximation for both longitudinal axis L and the looped fibers 8 can be used for determining the angle of looped fibers 8 from longitudinal axis L. For example, as shown in FIG. 4, one fiber 8a is shown emphasized by a heavy line, and its linear approximation 8b is shown as a dashed line. This fiber makes an angle of approximately 80 degrees with the longitudinal axis (measured counterclockwise from L).

The orientation of looped fibers 8 in the tufts 6 is to be contrasted with the fiber composition and orientation for first precursor web 20, which, for nonwoven webs is best described as having a substantially randomly-oriented fiber alignment. In a woven web embodiment, the orientation of the looped fibers 8 in tufts 6 could be the same as described above, but the fibers of first precursor web 20 would have the orientation associated with the particular weaving process used to make the web, e.g., a square weave pattern.

In the embodiment shown in FIG. 1 the longitudinal axes L of tufts 6 are generally aligned in the MD. Tufts 6 and, therefore, longitudinal axes L, can, in principle, be aligned in any orientation with respect to the MD or CD. Therefore, in general, it can be said that for each tuft 6, the looped aligned fibers 8 are aligned generally orthogonal to the longitudinal axis L such that they have a significant vector component parallel to transverse axis T, and more preferably a major vector component parallel to transverse axis T.

In some embodiments, due to the preferred method of forming tufts 6, as described below, another characteristic of tufts 6 comprising predominantly looped, aligned fibers 8, can be their generally open structure characterized by open void area 10 defined interiorly of tufts 6, as shown in FIGS. 2 and 3. The void area 10 may have a shape that is wider or larger at the distal end 31 of the tuft 6 and narrower at the base 17 of the tuft 6. This is opposite to the shape of the tooth which is used to form the tuft 6. By "void area" is not meant an area completely free of any fibers; the term is meant as a general description of the general appearance of tufts 6. Therefore, it may be that in some tufts 6 a loose fiber 18 or a plurality of loose fibers 18 may be present in the void area 10. By "open" void area is meant that the two longitudinal ends of tuft 6 are generally open and free of fibers, such that tuft 6 can form something like a "tunnel" structure in an uncompressed state, as shown in FIG. 3.

Additionally, as a consequence of a preferred method of making web 1, the second side 5 of web 1 exhibits discontinuities 16 characterized by a generally linear indentation defined by formerly random fibers of the second surface 14 of first precursor web 20 having been urged directionally (i.e., in the "Z-direction" generally orthogonal to the MD-CD plane as shown in FIGS. 1 and 3) into tufts 6 by the teeth of the forming structure, described in detail below. The abrupt change of orientation exhibited by the previously randomly-oriented fibers of first precursor web 20 defines the discontinuity 16, which exhibits a linearity such that it can be described as having a longitudinal axis generally parallel to longitudinal axis L of the tuft 6. Due to the nature of many nonwoven webs useful as first precursor webs 20, discontinuity 16 may not be as distinctly noticeable as tufts 6. For this reason, the discontinuities 16 on the second side 5 of web 1 can go unnoticed and may be generally undetected unless web 1 is closely inspected. As such, the second side 5 of web 1 can have the look and feel of an un-tufted first precursor web 20. Thus in some embodiments, web 1 can have the textured look and feel of terry cloth on first side 3, and a relatively smooth, soft look and feel on second side 5, both sides being comprised of fibers from the same nonwoven web, i.e., the first precursor web 20. In other embodiments, discontinuities 16 can appear as apertures, and may be apertures through web 1 via the ends of the tunnel-like tufts 6.

From the description of web 1 comprising a nonwoven first precursor web 20, it can be seen that the fibers 8 or 18 of tuft 6 can originate and extend from either the first surface 12 or the second surface 14 of first precursor web 20. Of course the fibers 8 or 18 of tuft 6 can also extend from the interior 28 of first precursor web 20. As shown in FIG. 3, the fibers 8 or 18 of tufts 6 extend due to having been urged out of the generally two-dimensional plane of first precursor web 20 (i.e., urged in the "Z-direction" as shown in FIG. 3). In general, the fibers 8 or 18 of the tufts 6 comprise fibers that are integral with and extend from the fibers of the first precursor web 20.

Therefore, from the above description, it is understood that in one embodiment web 1 can be described as being a laminate web formed by selective mechanical deformation of at least a first and second precursor webs, at least the first precursor web being a nonwoven web, the laminate web having a first side, the first side comprising the second precursor web and a plurality of discrete tufts, each of the discrete tufts comprising a plurality of tufted fibers being integral extensions of the first precursor web and extending through the second precursor web; and a second side, the second side comprising the first precursor web.

The extension of fibers 8 or 18 can be accompanied by a general reduction in fiber cross sectional dimension (e.g., diameter for round fibers) due to plastic deformation of the fibers and Poisson's ratio effects. Therefore, the aligned looped fibers 8 of tuft 6 can have an average fiber diameter less than the average fiber diameter of the fibers of first precursor web 20. It is believed that this reduction in fiber diameter contributes to the perceived softness of the first side 3 of web 1, a softness that can be comparable to cotton terry cloth, depending on the material properties of the first precursor web 20. It has been found that the reduction in fiber cross-sectional dimension is greatest intermediate the base 17 and the distal portion 31 of tuft 6. This is believed to be due to the preferred method of making, as disclosed more fully below. Briefly, as shown on FIG. 3, it is believed that portions of fibers at the base 17 and distal portion 31 of tufts 6 are adjacent the tip of teeth 110 of roll 104, described more fully below, and are frictionally locked and immobile during processing. Thus, the intermediate portions of tufts 6 are more free to stretch, or elongate, and accordingly, can experience a corresponding fiber cross sectional dimension reduction. Some fibers of first precursor web 20 may laterally squeeze the base 17 of the tuft 6. The base 17 of the tuft 6 may even be closed (if the fibers from the tuft 6 are close enough together to touch) or may remain open. Generally, any opening at the base 17 is narrow. The closing or narrowing or squeezing of other fibers at the base 17 can help to stabilize the tufts 6 and second precursor web 21.

Figure 5:
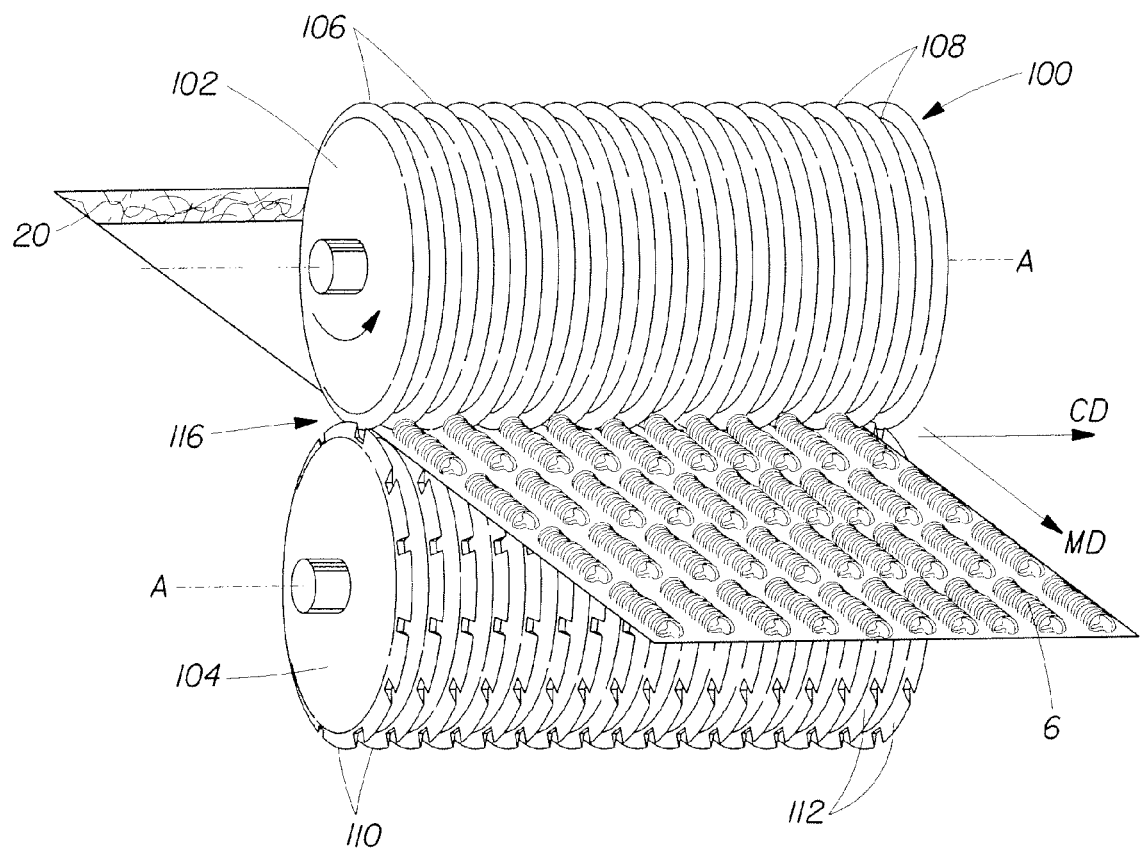
FIG. 5 is a perspective view of an apparatus for forming the web of the present invention.

Referring to FIG. 5 there is shown in an apparatus and method for making web 1 of the present invention. The apparatus 100 comprises a pair of intermeshing rolls 102 and 104, each rotating about an axis A, the axes A being parallel in the same plane. Roll 102 comprises a plurality of ridges 106 and corresponding grooves 108 which extend unbroken about the entire circumference of roll 102. Roll 104 is similar to roll 102, but rather than having ridges that extend unbroken about the entire circumference, roll 104 comprises a plurality of rows of circumferentially-extending ridges that have been modified to be rows of circumferentially-spaced teeth 110 that extend in spaced relationship about at least a portion of roll 104. The individual rows of teeth 110 of roll 104 are separated by corresponding grooves 112. In operation, rolls 102 and 104 intermesh such that the ridges 106 of roll 102 extend into the grooves 112 of roll 104 and the teeth 110 of roll 104 extend into the grooves 108 of roll 102. The intermeshing is shown in greater detail in the cross sectional representation of FIG. 6, discussed below. Both or either of rolls 102 and 104 can be heated by means known in the art such as by using hot oil filled rollers or electrically-heated rollers.

In FIG. 5, the apparatus 100 is shown in a preferred configuration having one patterned roll, e.g., roll 104, and one non-patterned grooved roll 102. However, in certain embodiments it may be preferable to use two patterned rolls 104 having either the same or differing patterns, in the same or different corresponding regions of the respective rolls. Such an apparatus can produce webs with tufts 6 protruding from both sides of the web 1. An apparatus could also be designed to have teeth that pointing in opposite directions on the same roll. This would result in a web with tufts 6 being produced on both sides of the web.

The method of making a web 1 of the present invention in a commercially viable continuous process is depicted in FIG. 5. Web 1 is made by mechanically deforming precursor webs, such as first and second precursor webs, 20 and 21 that can each be described as generally planar and two dimensional prior to processing by the apparatus shown in FIG. 5. By "planar" and "two dimensional" is meant simply that the webs start the process in a generally flat condition relative to the finished web 1 that has distinct, out-of-plane, Z-direction three-dimensionality due to the formation of tufts 6. "Planar" and "two-dimensional" are not meant to imply any particular flatness, smoothness or dimensionality.

The process and apparatus of the present invention is similar in many respects to a process described in U.S. Pat. No.

5,518,801 entitled "Web Materials Exhibiting Elastic-Like Behavior" and referred to in subsequent patent literature as "SELF" webs, which stands for "Structural Elastic-like Film". However, there are significant differences between the apparatus and process of the present invention and the apparatus and process disclosed in the '801 patent, and the differences are apparent in the respective webs produced thereby. As described below, the teeth 110 of roll 104 have a specific geometry associated with the leading and trailing edges that permit the teeth to essentially "punch" through the precursor webs 20, 21 as opposed to, in essence, deforming the web. In a two layer laminate web 1 the teeth 110 urge fibers from a first precursor web 20 simultaneously out-of-plane and through second precursor web 21, which is punctured, so to speak, by the teeth 110 pushing the fibers 8 through to form tufts 6. Therefore, a web 1 of the present invention can have tufts 6 of loose fiber ends 18 and/or "tunnel-like" tufts 6 of looped, aligned fibers 8 extending through and away from the surface 13 of a first side 3, unlike the "tent-like" rib-like elements of SELF webs which each have continuous side walls associated therewith, i.e., a continuous "transition zone," and which do not exhibit interpenetration of one layer through another layer.

Precursor webs 20 and 21 are provided either directly from their respective web making processes or indirectly from supply rolls (neither shown) and moved in the machine direction to the nip 116 of counter-rotating intermeshing rolls 102 and 104. The precursor webs are preferably held in a sufficient web tension so as to enter the nip 16 in a generally flattened condition by means well known in the art of web handling. As each precursor web 20, 21 goes through the nip 116 the teeth 110 of roll 104 which are intermeshed with grooves 108 of roll 102 simultaneously urge portions of first precursor web 20 out of the plane of first precursor web 20 and through second precursor web 21 to form tufts 6. In effect, teeth 110 "push" or "punch" fibers of first precursor web 20 through second precursor web 21.

As the tip of teeth 110 push through first and second precursor webs 20, 21 the portions of the fibers of first precursor web 20 that are oriented predominantly in the CD across teeth 110 are urged by the teeth 110 out of the plane of first precursor web 20. Fibers can be urged out of plane due to fiber mobility, or they can be urged out of plane by being stretched and/or plastically deformed in the Z-direction. Portions of first precursor web 20 urged out of plane by teeth 110 push through second precursor web 21, which due to its relatively lower extensibility, ruptures, thereby resulting in formation of tufts 6 on first side 3 of web 1. Fibers of first precursor web 20 that are predominantly oriented generally parallel to the longitudinal axis L, i.e., in the MD of precursor web 20 as shown in FIG. 1, are simply spread apart by teeth 110 and remain substantially in their original, randomly-oriented condition. This is why the looped fibers 8 can exhibit the unique fiber orientation in embodiments such as the one shown in FIGS. 1-4, which is a high percentage of fibers of each tuft 6 having a significant or major vector component parallel to the transverse axis T of tuft 6.

It can be appreciated by the forgoing description that when web 1 is made by the apparatus and method of the present invention that the precursor webs 20, 21 should possess differing material properties with respect to the ability of the precursor webs to elongate before failure, e.g., failure due to tensile stresses. In particular, a nonwoven first precursor web 20 can have greater fiber mobility and/or greater fiber elongation characteristics relative to second precursor web 21, such that the fibers thereof can move or stretch sufficiently to form tufts 6 while the second precursor web 21 ruptures, i.e., does not stretch to the extent necessary to form tufts.

The degree to which the fibers of nonwoven precursor webs are able to extend out of plane without plastic deformation can depend upon the degree of inter-fiber bonding of the precursor web. For example, if the fibers of a nonwoven precursor web are only very loosely entangled to each other, they will be more able to slip by each other (i.e., to move relative to adjacent fibers by reptation) and therefore be more easily extended out of plane to form tufts. On the other hand, fibers of a nonwoven precursor web that are more strongly bonded, for example by high levels of thermal point bonding, hydroentanglement, or the like, will more likely require greater degrees of plastic deformation in extended out-of-plane tufts. Therefore, in one embodiment, first precursor web 20 can be a nonwoven web having relatively low inter-fiber bonding, and second precursor web 21 can be a nonwoven web having relatively high inter-fiber bonding, such that the fibers of first precursor web can extend out of plane, while the fibers of second precursor web 21 cannot. Upon sufficient force applied to first precursor web 21, the fibers therein tend to extend, while the fibers of second precursor web, unable to extend, tend to break.

For a given maximum strain (e.g., the strain imposed by teeth 110 of apparatus 100), second precursor web 21 must actually fail under the tensile loading produced by the imposed strain. That is, for the tufts 6 of the present invention to be disposed on the first side 3 of web 1, second precursor web 21 must have sufficiently low fiber mobility (if any) and/or relatively low elongation-to-break such that it locally (i.e., in the area of strain) fails in tension, thereby producing openings 4 through which tufts 6 can extend. If second precursor web 21 merely deforms or stretches in the region of induced strain, but does not actually fail, thereby producing an opening 4 therein, a tuft 6 may not result. In one embodiment second precursor web 21 has an elongation to break in the range of 1%-5%. While the actual required elongation to break depends on the strain to be induced to form web 1, it is recognized that for most embodiments, second precursor web 21 can exhibit a web elongation-to-break of 6%, 7%, 8%, 9%, 10%, or more. It is also recognized that actual elongation-to-break can depend on the strain rate, which, for the apparatus shown in FIG. 5 is a function of line speed. Elongation to break of webs used in the present invention can be measured by means known in the art, such as by standard tensile testing methods using standard tensile testing apparatuses, such as those manufactured by Instron, MTS, Thwing-Albert, and the like.

Furthermore, relative to first precursor web 20, second precursor web 21 should have lower fiber mobility (if any) and/or lower elongation-to-break (i.e., elongation-to-break of individual fibers, or, if a film, elongation-to-break of the film) such that, rather than extending out-of-plane to the extent of the tufts 6, second precursor web 21 fails in tension under the strain produced by the formation of tufts 6, e.g., by the teeth 110 of apparatus 100. In one embodiment, second precursor web 21 exhibits sufficiently low elongation-to-break relative to first precursor web 20 such that flaps 7 of opening 4 only extend slightly out-of-plane, if at all, relative to tufts 6. In general, it is believed that second precursor web 21 should have an elongation to break of at least 10% less than the first precursor web 20, preferably at least 30% less, more preferably at least 50% less, and even more preferably at least about 100% less than that of first precursor web 20. Relative elongation to break values of webs used in the present invention can be measured by means known in the art, such as by standard tensile testing methods using standard tensile testing apparatuses, such as those manufactured by Instron, MTS, Thwing-Albert, and the like.

In one embodiment second precursor web 21 can comprise substantially all MD-oriented fibers, e.g., tow fibers, such that there are substantially no fibers oriented in the CD. For such an embodiment of web 1 the fibers of second precursor web 21 can simply separate at the opening 4 through which tufts 6 extend. In this embodiment, therefore, second precursor web 21 need not have any minimum elongation to break, since failure or rupture of the material is not the mode of forming opening 4.

The number, spacing, and size of tufts 6 can be varied by changing the number, spacing, and size of teeth 110 and making corresponding dimensional changes as necessary to roll 104 and/or roll 102. This variation, together with the variation possible in precursor webs 20, 21 permits many varied webs 1 to be made for many purposes. For example, web 1 made from a first precursor web 20 comprising a relatively high basis weight woven fabric having MD and CD woven plastically-extensible threads and a second precursor web 21 comprising relatively high basis weight, relatively low-extensible synthetic polymer nonwoven material could be made into a strong, porous ground covering, such as an erosion control device useful for reducing sloping path deterioration and enabling growth of indigenous vegetation in unstable soil. A web 1 made from a first precursor web 20 comprising a relatively low basis weight nonwoven web of plastically-extensible spunbond polymer fibers and a second precursor web 21 comprising relatively low-extensible synthetic polymer film could be could be used as a terry cloth-like fabric for semi-durable or durable clothing, or for personal care items as are described in WO 01/76523. As described more fully below, a web 1 comprising a nonwoven/film first precursor web/second precursor web combination can also be used as a component in disposable absorbent articles.

Figure 6:
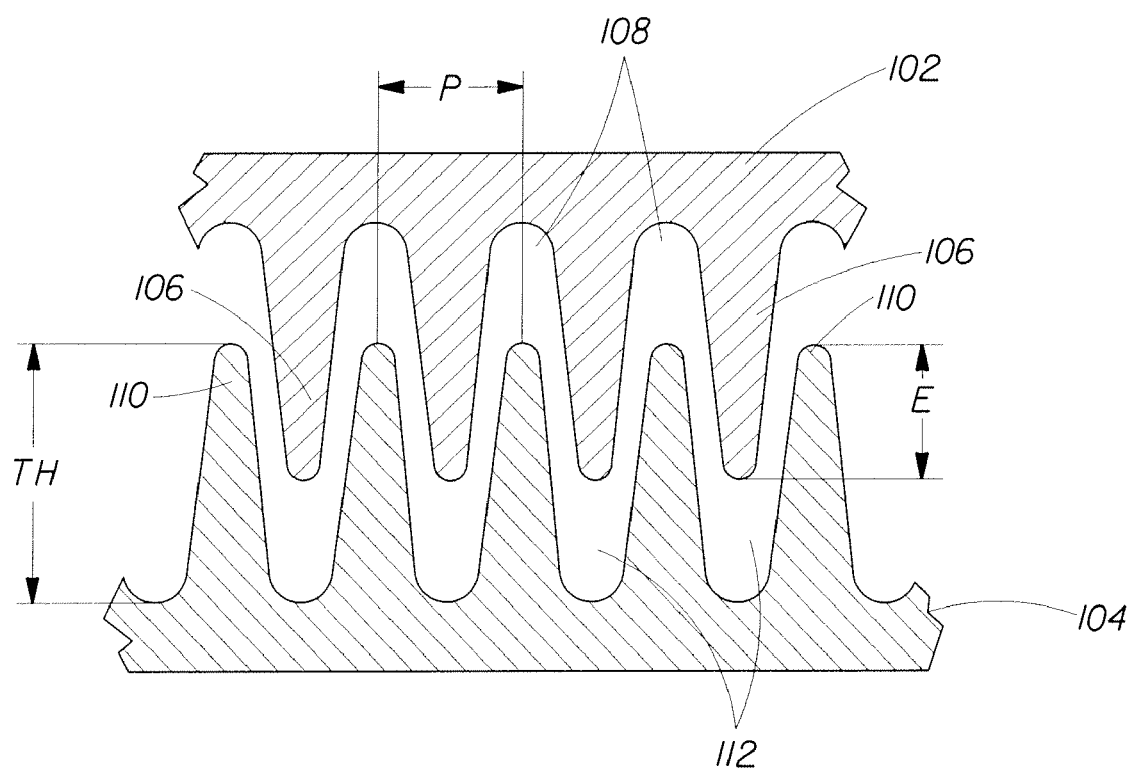
FIG. 6 is a cross-sectional depiction of a portion of the apparatus shown in FIG. 5.

FIG. 6 shows in cross section a portion of the intermeshing rolls 102 and 104 and ridges 106 and teeth 110. As shown teeth 110 have a tooth height TH (note that TH can also be applied to ridge height; in a preferred embodiment tooth height and ridge height are equal), and a tooth-to-tooth spacing (or ridge-to-ridge spacing) referred to as the pitch P. As shown, depth of engagement E is a measure of the level of intermeshing of rolls 102 and 104 and is measured from tip of ridge 106 to tip of tooth 110. The depth of engagement E, tooth height TH, and pitch P can be varied as desired depending on the properties of precursor webs 20, 21 and the desired characteristics of web 1. For example, in general, the greater the level of engagement E, the greater the necessary elongation or fiber-to-fiber mobility characteristics the fibers of first precursor web 20 must possess. Also, the greater the density of tufts 6 desired (tufts 6 per unit area of web 1), the smaller the pitch should be, and the smaller the tooth length TL and tooth distance TD should be, as described below.

Figure 7:
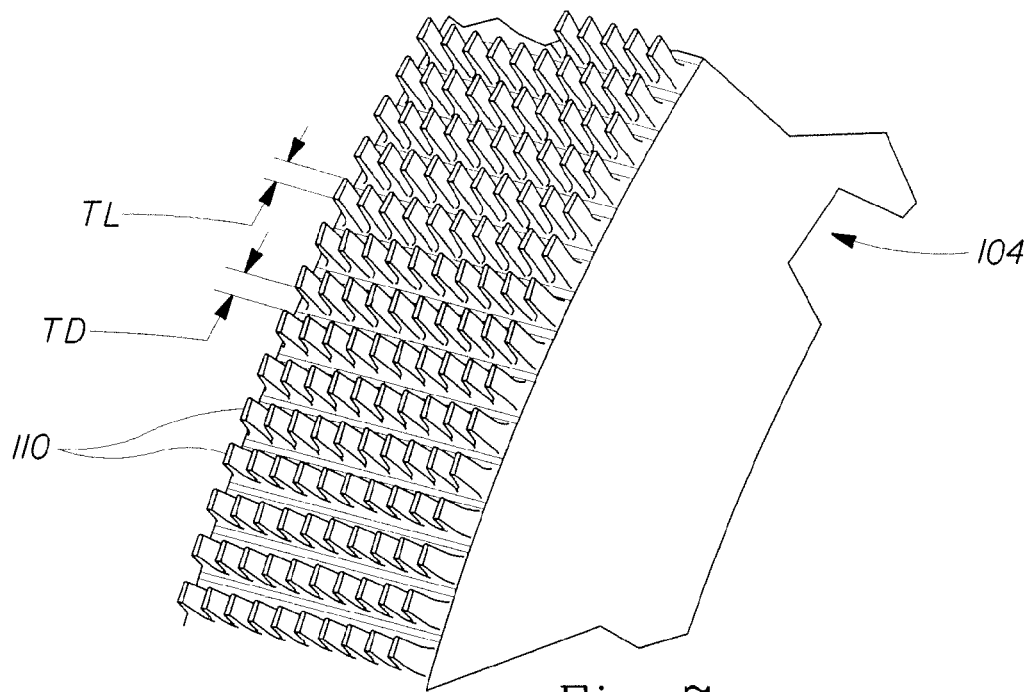
FIG. 7 is a perspective view of a portion of the apparatus for forming one embodiment the web of the present invention.

FIG. 7 shows one embodiment of a roll 104 having a plurality of teeth 110 useful for making a terry cloth-like web 1 from a nonwoven first precursor web 20 having a basis weight of between about 60 gsm and 100 gsm, preferably about 80 gsm and a polyolefinic film (e.g., polyethylene or polypropylene) second precursor web 21 having a density of about 0.91-0.94 and a basis weight of about 20 gsm.

Figure 8:
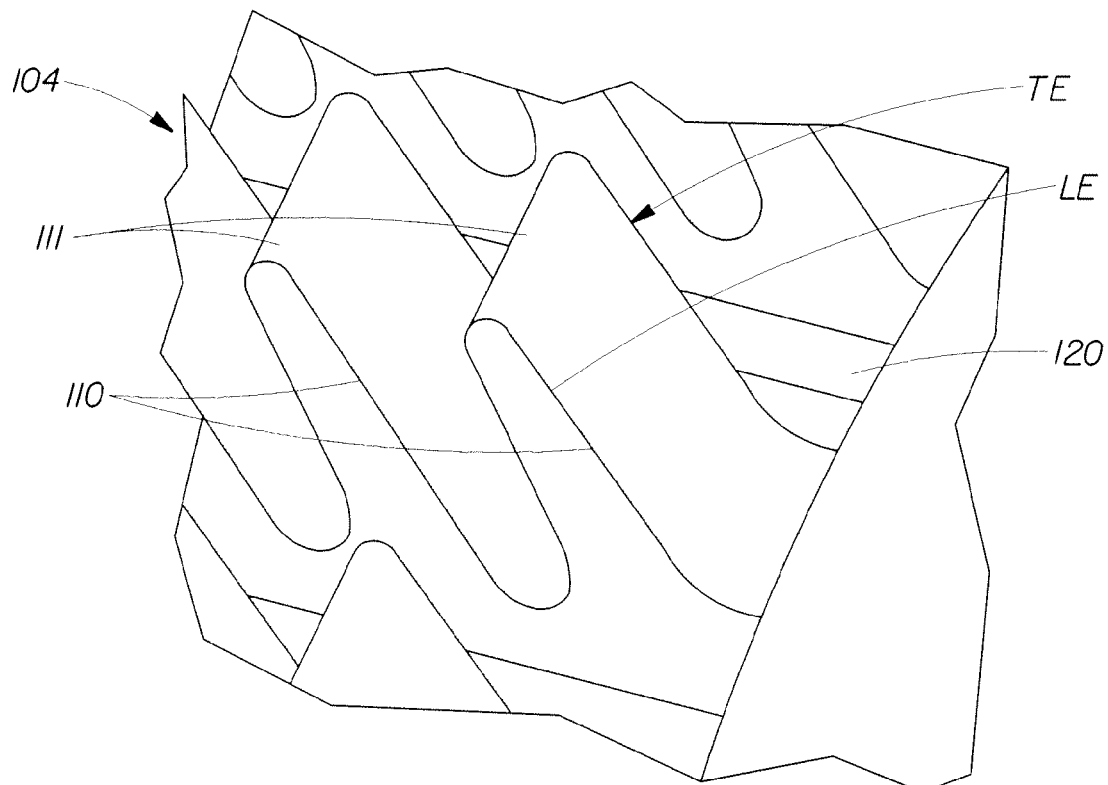
FIG. 8 is an enlarged perspective view of a portion of the apparatus for forming the web of the present invention.

An enlarged view of teeth 110 is shown in FIG. 8. In this embodiment of roll 104 teeth 110 have a uniform circumferential length dimension TL measured generally from the leading edge LE to the trailing edge TE at the tooth tip 111 of about 1.25 mm and are uniformly spaced from one another circumferentially by a distance TD of about 1.5 mm. For making a terry-cloth web 1 from web 1 having a total basis weight in the range of about 60 to about 100 gsm, teeth 110 of roll 104 can have a length TL ranging from about 0.5 mm to about 3 mm and a spacing TD from about 0.5 mm to about 3 mm, a tooth height TH ranging from about 0.5 mm to about 5 mm, and a pitch P between about 1 mm (0.040 inches) and about 5 mm (0.200 inches). Depth of engagement E can be from about 0.5 mm to about 5 mm (up to a maximum equal to tooth height TH). Of course, E, P, TH, TD and TL can be varied independently of each other to achieve a desired size, spacing, and area density of tufts 6 (number of tufts 6 per unit area of web 1).

As shown in FIG. 8, each tooth 110 has a tip 111, a leading edge LE and a trailing edge TE. The tooth tip 111 is elongated and has a generally longitudinal orientation, corresponding to the longitudinal axes L of tufts 6 and discontinuities 16. It is believed that to get the tufted, looped tufts 6 of the web 1 that can be described as being terry cloth-like, the LE and TE should be very nearly orthogonal to the local peripheral surface 120 of roll 104. As well, the transition from the tip 111 and LE or TE should be a sharp angle, such as a right angle, having a sufficiently small radius of curvature such that teeth 110 push through second precursor web 21 at the LE and TE. Without being bound by theory, it is believed that having relatively sharply angled tip transitions between the tip of tooth 110 and the LE and TE permits the teeth 110 to punch through precursor webs 20, 21 "cleanly", that is, locally and distinctly, so that the first side 3 of the resulting web 1 can be described as "tufted" rather than "deformed." When so processed, the web 1 is not imparted with any particular elasticity, beyond what the precursor webs 20 and 21 may have possessed originally. The punching through of the precursor web 21 may result in a small portion of the web 21 forming "confetti" or small pieces.

Figure 9:
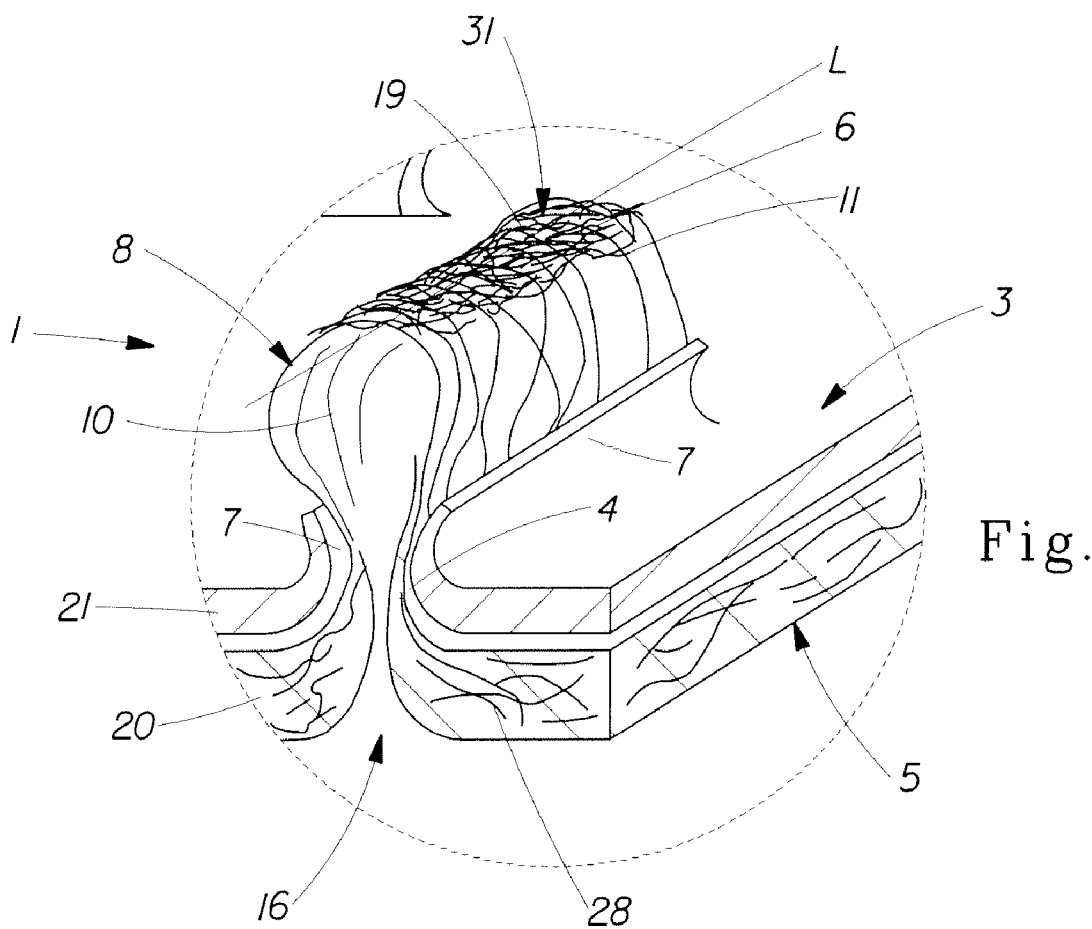
FIG. 9 is an enlarged view of a portion of another embodiment of a web of the present invention.

At higher line speeds, i.e., relatively higher rates of processing of the web through the nip of rotating rolls 102 and 104, like materials can exhibit very different structures for tufts 6. The tuft 6 shown in FIG. 9 is similar in structure to the tuft shown in FIG. 2 but exhibits a very different structure, a structure that appears to be typical of spunbond nonwoven materials processed to form tufts 6 at relatively high speeds, i.e., at high strain rates. Typical of this structure is broken fibers between the proximal portion, i.e., base 17, of tufts 6 and the distal portion, i.e., the top 31, of tuft 6, and what appears to be a "mat" 19 of fibers at the top of the tuft 6. Mat 19 comprises and is supported at the top of tufts 6 by unbroken, looped fibers 8, and also comprises portions of broken fibers 11 that are no longer integral with first precursor web 20. That is, mat 19 comprises fiber portions which were formerly integral with precursor web 20 but which are completely detached from precursor web 20 after processing at sufficiently high line speeds, e.g., 30 meters per minute line speed in the process described with reference to FIG. 5.

Therefore, from the above description, it is understood that in one embodiment web 1 can be described as being a laminate web formed by selective mechanical deformation of at least a first and second precursor webs, at least the first precursor web being a nonwoven web, the laminate web having a first side, the first side comprising the second precursor web and a plurality of discrete tufts, each of the discrete tufts comprising fibers integral with but extending from the first precursor web and fibers neither integral with nor extending from the first precursor web.

Although it is believed that the distinct fiber orientation observed at the distal portion 31 of tufts 6, e.g., mat 19, is due primarily to processing rates, it is also believed to be affected by other parameters, such as fiber type and basis weight of the first precursor web 20 as well as processing temperatures that can affect the degree of fiber-to-fiber bonding. Matting of fibers is believed to occur on the portion of tuft 6 associated during manufacturing with the tip of tooth 110 of roll 104. It is believed that frictional engagement of the fibers at the tip of the teeth "lock" the fibers in place, thereby limiting fiber elongation and/or fiber mobility, two mechanisms believed to permit formation of tufts 6. Therefore, once locked, so to speak, in position, fibers adjacent tooth 110 tip can be broken, and, due to the random entanglement of the precursor web as well as possible cold welding of fibers due to pressure and friction, the broken fibers 11 become and remain lodged in mat 19 at the distal end 31 of tufts 6.

First precursor webs 20 having relatively higher basis weights generally have relatively more fiber 11 portions in mat 19. In one sense, it appears as if most of the fiber content of the first precursor web 20 in the immediate vicinity of a tooth tip 110 during manufacture is simply displaced in the Z-direction to the distal portion 31 of tufts 6, resulting in mat 19. First precursor webs 20 comprising relatively low elongation fibers, or fibers with relatively low fiber-to-fiber mobility (e.g., relatively limited capability for fiber reptation) appear to result in relatively few fibers becoming and remaining lodged in mat 19 at the distal end 31 of tufts 6. Fiber-to-fiber mobility can be increased by reducing or eliminating the fiber-to-fiber bonds. Thermal bonds can be completely eliminated (i.e., avoided by not bonding), or significantly reduced in certain nonwoven webs to increase fiber-to-fiber mobility. Similarly, hydroentangled webs can be less entangled to increase fiber-to-fiber mobility. For any precursor web 20, lubricating it prior to processing as disclosed herein can also increase fiber-to-fiber mobility. For example, a mineral oil lubricant can be applied to first precursor web 20 prior to it entering the nip 116 of rolls 102 and 104. Additionally, a plasticizing agent, such as petrolatum, can be added to some synthetic fiber webs, such as polyethylene or a polyethylene and polypropylene web, to increase extensibility.

The result of the presence of mats 19 is a web 1 having a slightly rougher, textured impression on one side thereof, useful, for example, for wipes in which more scrubbing texture is desirable. In one sense a web having soft terry cloth-like tactile impression when made under relatively low-speed processing conditions, can have relatively abrasive feel when processed under identical, but relatively higher line speed conditions. This rough, textured tactile impression on a fibrous web can be useful for some applications, such as for a hard surface cleaning wipe or an exfoliating facial wipe. Therefore, whether the web 1 is desired to be soft and cloth-like for use with a mucilaginous substance to be applied to inflamed parts of the body, e.g., a cataplasm, or as a conformable, semi-durable light abrasive for gently removing rust and oxidation from curved surfaces of metals, the rate of formation of tufts 6 can be adjusted to give the necessary texture.

While not wishing to be bound by theory, it is believed that if the fibers of the first precursor web have a highly curvilinear shape, e.g., curled fibers, the resultant tufts 6 will have more looped fibers 8 and less broken fibers 18 as compared to more linear fiber conformations. It is believed that such fiber conformations have a lesser chance of bridging between two adjacent teeth, and, as a result they are less prone to be stretched beyond their breaking point, and thus have a greater chance of forming complete loop structures. Furthermore, such curvilinear-shaped fibers can be made by using eccentric bicomponent fibers, or side-by-side bicomponent fibers, such as bicomponent fibers consisting of polyethylene and nylon.

It has been found that certain nonwoven webs, such as carded webs comprising staple-length fibers, when used as first precursor web 20 produce very few looped fibers 8 in tufts 6, so that the tufts 6 produced in these webs cannot be described as comprising a plurality of looped, aligned fibers 8 as described above with respect to FIGS. 1-4. Instead, carded nonwoven webs can produce tufts 6 having few, if any, looped, aligned fibers 8, and many, if not all, non-aligned fibers and/or broken fibers 18. It is believed that the non-alignment of fibers in tufts 6 made from carded webs is due in part to the nature of the fiber content of carded webs. Staple fibers are not "endless," but instead have a predetermined length on the order of about 15 mm to about 100 mm, and, more typically from about 40 mm to about 80 mm. Therefore, when a carded web is processed by the apparatus described with respect to FIG. 5, it is believed that there is a much greater likelihood that a loose fiber end will be in the vicinity of a tuft 6 and thus produce a non-looped fiber end in tuft 6. Furthermore, often staple fibers do not have the same elongation characteristics of spunbond or meltblown fibers, for example. However, even if tufts 6 have no looped fibers, the fibrous tufts can nevertheless provide a softness benefit and produce a web having terry cloth-like characteristics.

Therefore, from the above description, it is understood that in one embodiment web 1 can be described as being a laminate web formed by selective mechanical deformation of at least a first and second precursor webs, at least the first precursor web being a nonwoven web, the laminate web having a first side, the first side comprising the second precursor web and a plurality of discrete tufts, the tufts comprising a plurality of fibers integral with but extending from said first region.

If a woven first precursor web 20 is utilized, the formation and structure of tufts 6 can be very close to the same as that exhibited by tufts 6 formed from nonwoven webs. For example, if a woven first precursor web 20 has extensible warp and/or weft threads predominantly oriented in a cross machine direction, upon being processed by the apparatus 100 described above, the teeth 110 tend to separate the machine direction threads (either warp or weft) and only urge out of plane the cross-machine direction threads. Thus, the web 1 produced from a woven first precursor web 20 can look and feel very much like terry cloth fabric.

In preferred embodiments first precursor web 20 is a nonwoven web in which there are minimal fiber-to-fiber bonds. For example, the precursor web can be a nonwoven web having a pattern of discrete thermal point bonds, as is commonly known in the art for nonwoven webs. In general, however, it is desirable to minimize the number of bond points and maximize the spacing so as to allow for maximum fiber mobility and dislocation at during formation of tufts 6. In general, utilizing fibers having relatively high diameters, and/or relatively high extension to break, and/or relatively high fiber mobility, results in better and more distinctly formed tufts 6.

Although web 1 is disclosed in preferred embodiments as a two layer web made from two precursor webs, it is not necessary that it be limited to two layers. For example, a three-layer or more laminate can be made from three precursor webs, as long as one of the precursor webs can extend and push through openings in another layer to form tufts. For example, web 1 could comprise the top sheet, secondary topsheet, and core of hygiene products. In general, it is not necessary that adhesive or other bonding means be utilized to make laminate web 1.

The constituent layers of web 1 (e.g., precursor webs 20 and 21 and any other layers) can be held in a face-to-face laminated relationship by virtue of the "locking" effect of the tufts 6 that extend through openings 4 in second precursor web 21. In some embodiments it may be desirable to use adhesives or thermal bonding or other bonding means, depending on the end use application of web 1. For example, a web 1 comprising bicomponent fiber nonwoven webs can be through-air bonded after formation of tufts 6 to provide for layer-to-layer adhesion for greater peel strength. Additionally, it may be desirable to apply adhesive to at least a portion of one of the precursor webs. For example, in some embodiments adhesive, chemical bonding, resin or powder bonding, or thermal bonding between layers can be selectively applied to certain regions or all of the precursor webs. In the case of adhesive application, for example, adhesive can be applied in a continuous manner, such as by slot coating, or in a discontinuous manner, such as by spraying, extruding, and the like. Discontinuous application of adhesive can be in the form of stripes, bands, droplets, and the like.

Although web 1 is disclosed in preferred embodiments as comprising a nonwoven first precursor web, in practice, any of the precursor webs can be nonwoven webs, polymer films, woven webs, or paper webs. Of course, regardless of the web characterization, the first precursor web must have sufficient material properties such as extensibility and yield-to-break to be locally deformed into discrete tufts. Likewise, the second precursor web must have relatively less extensibility or yield-to-break, such that it ruptures when processed according to the method disclosed herein.

In a multilayer web 1 each precursor web can have different material properties, thereby providing web 1 with beneficial properties. For example, web 1 comprising two (or more) precursor webs, e.g., first and second precursor webs, can have beneficial fluid handling properties for use as a topsheet on a disposable absorbent article, as described more fully below. For superior fluid handling, for example, first precursor web 20 can be comprised of relatively hydrophilic fibers. Second precursor web 21 can be polymer film, e.g., a polyethylene film, and can be hydrophobic or rendered hydrophobic. The tufts 6 of such a web could form an upper layer, i.e., a body-contacting layer when used as a topsheet on a disposable absorbent article. Fluid deposited upon the upper, relatively hydrophilic tufts is quickly transported away from the relatively hydrophobic film to the portion of the first precursor web underlying the second film precursor web layer. One reason for the observed rapid fluid transport is the capillary structures formed by the generally aligned fibers 8, 18 of tufts 6. The fibers 8, 18 form directionally-aligned capillaries between adjacent fibers, and the capillary action is enhanced by the general convergence of fibers near the base 17 of tufts 6.

It is believed that the rapid fluid transport is further increased due to the ability of fluid to enter the web 1 via the voids 10 defined by looped tufts 6. This "lateral entry" capability and/or capillary action, and/or the hydrophilicity gradient afforded by the structure of web 1 makes web 1 an ideal material for optimal fluid handling for disposable absorbent articles. In particular, a multilayer web 1 can provide for even greater improvement in fluid handling characteristics.

Depending on the precursor webs 20 and 21 utilized and the dimensional parameters of rolls 102 and, including teeth 110, web 1 of the present invention can exhibit a wide range of physical properties. The web 1 can exhibit a range of texture subjectively experienced as ranging from softness to roughness, an absorbency ranging from non-absorbent to very absorbent, a bulkiness ranging from relatively low bulk to relatively high bulk; a tear strength ranging from low tear strength to high tear strength; an elasticity ranging from non-elastic to at least 100% elastically extensible, a chemical resistance ranging from relatively low resistance to high resistance, depending on the chemical considered, and many other variable parameters generally described as shielding performance, alkali resistance, opacity, wiping performance, water absorptivity, oil absorptivity, moisture permeability, heat insulating properties, weatherability, high strength, high tear force, abrasion resistance, electrostatic controllability, drape, dye-effinity, safety and the like. In general, depending on the elongation properties of the first precursor web 20, the dimensions of apparatus 100 can be varied to produce a web 1 having a wide range of dimensions associated with tufts 6, including the height h (as shown in FIG. 3), and spacing (including area density of tufts 6). Additionally, the tufts may be easily patterned into lines, filled forms, and selective regions of the laminate web by having the desired pattern displayed in the teeth 110 on the roll 104.

Web 1 may be used for a wide variety of applications, including various filter sheets such as air filter, bag filter, liquid filter, vacuum filter, water drain filter, and bacterial shielding filter; sheets for various electric appliances such as capacitor separator paper, and floppy disk packaging material; various industrial sheets such as tacky adhesive tape base cloth, oil absorbing material, and paper felt; various wiper sheets such as wipers for homes, services and medical treatment, printing roll wiper, wiper for cleaning copying machine, baby wipers, and wiper for optical systems; various medicinal and sanitary sheets, such as surgical gown, gown, covering cloth, cap, mask, sheet, towel, gauze, base cloth for cataplasm, diaper, diaper liner, diaper cover, feminine napkin covers, feminine napkin or diaper acquisition layer (underneath the cover layer), diaper core, tampon liners, base cloth for adhesive plaster, wet towel, and tissue; various sheets for clothes, such as padding cloth, pad, jumper liner, and disposable underwear; various life material sheets such as base cloth for artificial leather and synthetic leather, table top, wall paper, blind, wrapping, and packages for drying agents, shopping bag, suit cover, and pillow cover; various agricultural sheets, such as ground covers and erosion control devices, cooling and sun light-shielding cloth, lining curtain, sheet for overall covering, light-shielding sheet, wrapping materials of pesticides, underlining paper of pots for seeding growth; various protection sheets such as fume prevention mask and dust prevention mask, laboratory gown, and dust preventive clothes; various sheets for civil engineering building, such as house wrap, drain material, filtering medium, separation material, overlay, roofing, tuft and carpet base cloth, wall interior material, soundproof or vibration reducing sheet, and curing sheet; and various automobile interior sheets, such as floor mat and trunk mat, molded ceiling material, head rest, and lining cloth, in addition to a separator sheet in alkaline batteries. Other uses include utilizing web 1 as a wipe for personal cleansing or hygiene, such as for a baby wipe, facial cloth or wipe, or body cloth.

In one embodiment, web 1 or a composite comprising web 1 can be utilized as a fecal material storage element. Web 1 can be utilized as a secondary topsheet or sublayer when it is disposed under an apertured web or film to accept and hold low viscosity feces or viscous bodily waste away from a wearer's skin after defecation. Embodiments of the present invention having larger total three dimensional volume within the web or between the tufts 6 generally provide a greater capacity for storage of low viscosity feces. Absorbent articles employing such fecal material storage elements, or sublayers, are described in U.S. Pat. Nos. 5,941,864; 5,957,906; 6,018,093; 6,010,491; 6,186,992; and 6,414,215, among others.

In one embodiment, web 1 comprises a nonwoven first precursor web 20 comprising a spunbond nonwoven having a basis weight of about 80 gsm, and comprising polyethylene/polypropylene (sheath/core) bicomponent fibers having an average diameter of about 33 microns, and a second precursor web comprising a polyethylene film having a basis weight of 20 gsm. In this embodiment, web 1 has about 24 tufts 6 per square centimeter, the tufts 6 having a plurality of looped, aligned fibers 8, each of which has an average fiber diameter of about 18 microns. A web of this type can be beneficially used as a topsheet for disposable absorbent articles, as shown below with reference to FIG. 10. For example, such a web 1 is fluid impermeable except in the regions of the tufts 6 which can wick fluid from the first side 3 of web 1 to the second side 5.

Figure 10:
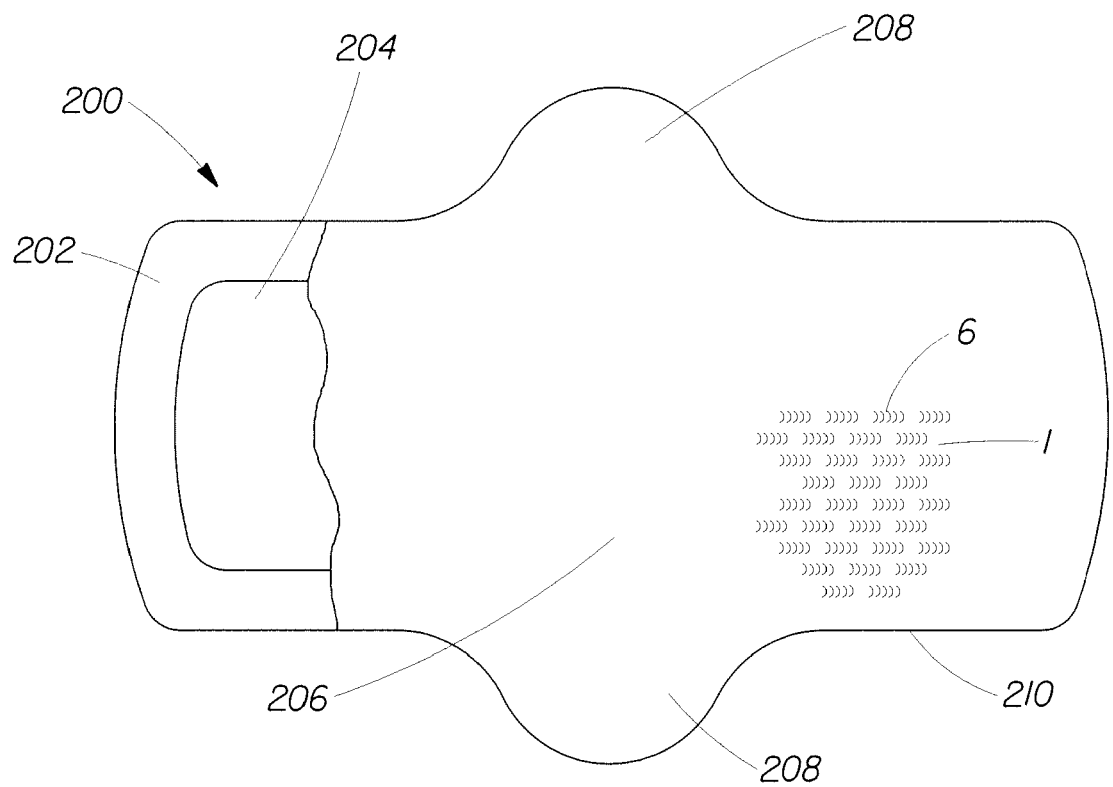
FIG. 10 is a partial cut away plan view of a sanitary napkin of the present invention.

FIG. 10 shows in partial cut away plan view a sanitary napkin having as one of its components a web 1 of the present invention. In general, sanitary napkin 200 comprises a backsheet 202, a topsheet 206 and an absorbent core 204 disposed between the topsheet 206 and backsheet 202 which can be joined about a the periphery 210. Sanitary napkin 1 can have side extensions, commonly referred to as "wings" 208 designed to wrap the sides of the crotch region of the panties of the user of sanitary napkin 1. Sanitary napkins, including topsheets for use as the body facing surface thereof, are well known in the art and need no detailed description of various alternative and optional designs. In addition to sanitary napkins, web 1 can also be used in a diaper or adult incontinence product or other disposable hygiene products. However, it is noted that web 1 can be used as, or as a component of, one or more of a backsheet, core material, topsheet, secondary topsheet, or wing material. Web 1 can also have multiple layers and comprise a topsheet, secondary topsheet, core, backsheet, or any number of layers.

Web 1 is especially useful as a topsheet 206 of sanitary napkin 200. Web 1 is particularly beneficial as a topsheet 206 for sanitary napkins due to the combination of excellent fluid acquisition and distribution to the absorbent core 204, and excellent prevention of rewet to the body-facing surface of topsheet 206 when in use. Rewet can be a result of at least two causes: (1) squeezing out of the absorbed fluid due to pressure on the sanitary napkin 200; and/or (2) wetness entrapped within or on the topsheet 206. In a preferred topsheet 206 both properties, fluid acquisition and fluid retention, are maximized and rewet is minimized. Said differently, preferably a topsheet will exhibit high rates of fluid acquisition, and low levels of rewet.

A topsheet 206 can be made by using a nonwoven first precursor web 20 and a fluid impermeable polyethylene film second precursor web 21. The basis weights of the component webs can be varied, however, in general due to cost and benefit considerations a total basis weight of between about 20 gsm and 80 gsm is desirable for web 1. When made as a film/nonwoven laminate, web 1 combines the softness and fluid capillarity of fiber tufts and the rewet prevention of a fluid impermeable polymer film. When a sanitary napkin is used having a topsheet 206 comprising web 1 with first side 3 being the body-facing side, and the second side 5 being in fluid communication with an underlying absorbent core, fluid can be acquired by tufts 6 on first side 3 of web 1 and wicked through second precursor web 21 to second side 5 of web 1 which can then be desorbed to the absorbent core 204. Because tufts 6 are discrete and spaced apart, and are separated by a fluid impermeable second precursor web 21, rewet can be minimized. Alternatively, web 1 could be used with first side 3 being the fluid communication side and second side 5 being the body-facing side. This enables the discontinuities 16 to potentially allow fluid to be transported into or through the tufts 6.

Figure 11:
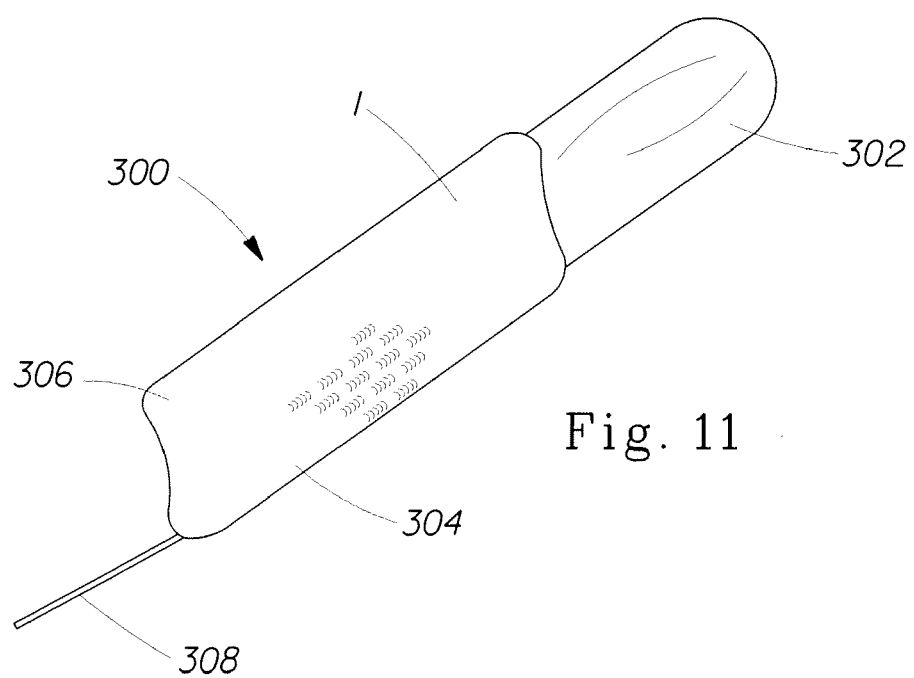
FIG. 11 is a partial cut away perspective view of a tampon of the present invention.

FIG. 11 shows in partial cut away perspective view a catamenial tampon 300 having as one of its components a web 1 of the present invention. In general, tampon 300 comprises a compressed absorbent core 302 and a fluid permeable cover wrap 304 that covers absorbent core 302. Cover wrap 304 may extend beyond one end of absorbent core 302 to form a skirt portion 306. A removal means, such as string 308 can be provided to facilitate removal of the tampon after use. Tampons, including cover wraps for use as the body contacting surface thereof, are well known in the art and need no detailed description of various alternative and optional designs. However, it is noted that web 1 can be used as, or as a component of, one or more of a cover wrap, absorbent core material, or removal means material.

Table 1 below shows representative examples of webs 1 according to the present invention, along with dimensions relative to the apparatus 100 used in the process to make them, as disclosed hereinabove. A brief description of each Sample listed follows Table 1.

TABLE 1

Examples of Apparatus Dimensional Parameters and Web Dimensions

| Sample No. | Precursor Web 1 | Precursor Web 2 | Precursor Web 3 | Pitch (P) \<mm\> (inches) | Engagement (E) \<mm\> (inches) | Tooth Height (TH) \<mm\> (inches) | Loop height (h) (mm) | Avg. Fiber Diameter of Precursor Web 1 (μm) | Avg. Fiber Diameter of Loop Fiber (μm) |
|---|---|---|---|---|---|---|---|---|---|
| 1 | Carded PET nonwoven web | LDPE Film | N/A | <1.5> (0.060) | <3.4> (0.135) | <3.7> (0.145) | 1.59 | 20 | 18 |
| 2 | Spunbond PE/PP core/sheath nonwoven web | Aluminum foil | N/A | <1.5> (0.060) | <3.4> (0.135) | <3.7> (0.145) | 1.37 | 24 | 13 |
| 3 | Spunbond PE/PP core/sheath nonwoven web | 30 lb Kraft paper | N/A | <1.5> (0.060) | <3.4> (0.135) | <3.7> (0.145) | 1.38 | 24 | 13 |

TABLE 1-continued

Examples of Apparatus Dimensional Parameters and Web Dimensions

| Sample No. | Precursor Web 1 | Precursor Web 2 | Precursor Web 3 | Pitch (P) <mm> (inches) | Engagement (E) <mm> (inches) | Tooth Height (TH) <mm> (inches) | Loop height (h) (mm) | Avg. Fiber Diameter of Precursor Web 1 (μm) | Avg. Fiber Diameter of Loop Fiber (μm) |
|---|---|---|---|---|---|---|---|---|---|
| 4 | Spunbonded PP nonwoven web | Airlaid PET nonwoven web | Spunbonded PP nonwoven web | <1.5> (0.060) | <3.4> (0.135) | <3.7> (0.145) | 1.83 | 34 | 28 |
| 5 | Spunbonded PP nonwoven web | Bounty paper towel | Spunbonded PP nonwoven web | <1.5> (0.060) | <3.4> (0.135) | <3.7> (0.145) | 1.8 | 34 | |

Figure 12:
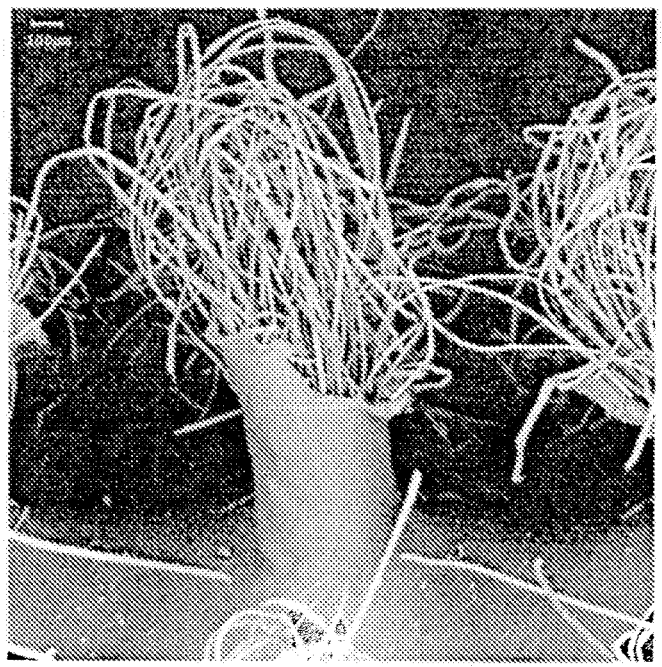
FIGS. 12-15 are photomicrographs of a webs of the present invention.

FIG. 12 is a photomicrograph of Sample 1. The first precursor web of Sample 1 was a carded PET nonwoven web having a basis weight of 145 grams per square meter (gsm) that was hand carded from 38 mm (1.5 inch) staple length polyester/co-polyester trilobal-shaped fibers, type F30A, from FIT (Fiber Innovation Technology) Inc., Johnson City, Tenn. The second precursor web of Sample 1 was a low density polyethylene (LDPE) film having a caliper of 0.1 mm (0.004 inch) made by Huntsman Film Products Co., Carrolton Ohio, designated as X420. Sample 1 was produced on an apparatus as described above with respect to FIG. 5 at a line speed of approximately 3 meters per minute (10 feet per minute). As shown in FIG. 12, flap 7 extends about significantly out of the plane of the second precursor web (i.e., the film layer) and covers approximately half of the tuft 6. As noted above, this can be desirable where a more stiff, resilient tuft 6 is desired.

Figure 13:
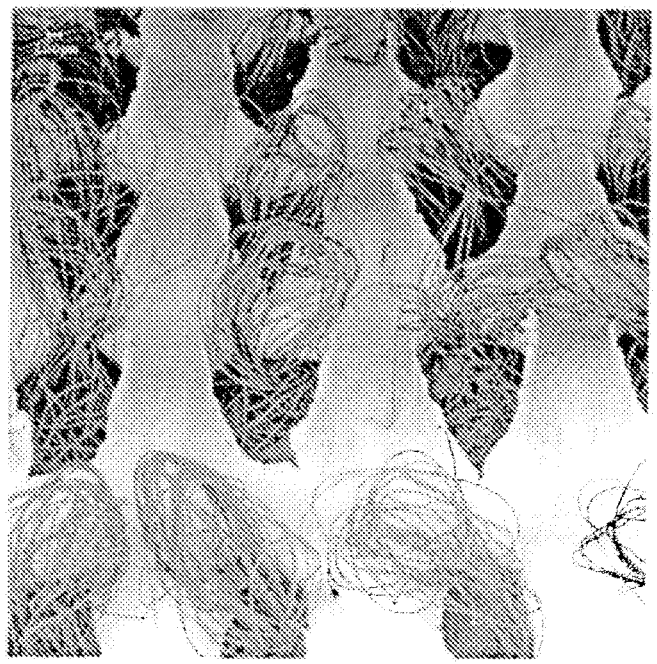

FIG. 13 is a photomicrograph of Sample 2. The first precursor web of Sample 2 was a spunbond PE/PP 50/50 core/sheath nonwoven web having a basis weight of 30 gsm and was made by BBA, Simpsonville S.C. The second precursor web of Sample 2 was aluminum foil obtained by removing (i.e., by rubbing) the adhesive off of Fasson® 1803 aluminum foil tape from Avery Dennison, U.S. Specialty Tape Division, Painesville Ohio. Sample 2 was produced on an apparatus as described above with respect to FIG. 5 at a line speed of approximately 3 meters per minute (10 feet per minute). As shown in FIG. 13, aluminum foil tends to split open, with very little plastic deformation of flaps 7.

Figure 14:
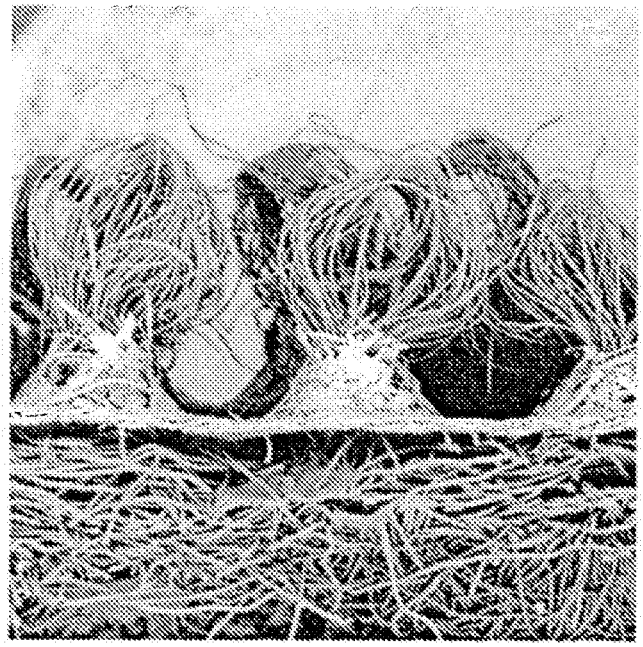

FIG. 14 is a photomicrograph of Sample 3. The first precursor web of Sample 3 is a spunbond PE/PP 50/50 core/sheath nonwoven having a basis weight of 30 gsm and was made by BBA, Simpsonville S.C. The second precursor web of Sample 3 was brown 100% recycled 30 lb Kraft packaging paper available from any source of Kraft paper, e.g., Uline Shipping Supplies, Waukegan, Ill. Sample 3 was produced on an apparatus as described above with respect to FIG. 5 at a line speed of approximately 3 meters per minute (10 feet per minute). As shown in FIG. 14, a second precursor web of Kraft paper can result in openings 4 and flaps 7 that resemble a volcano-shaped opening.

Figure 15:
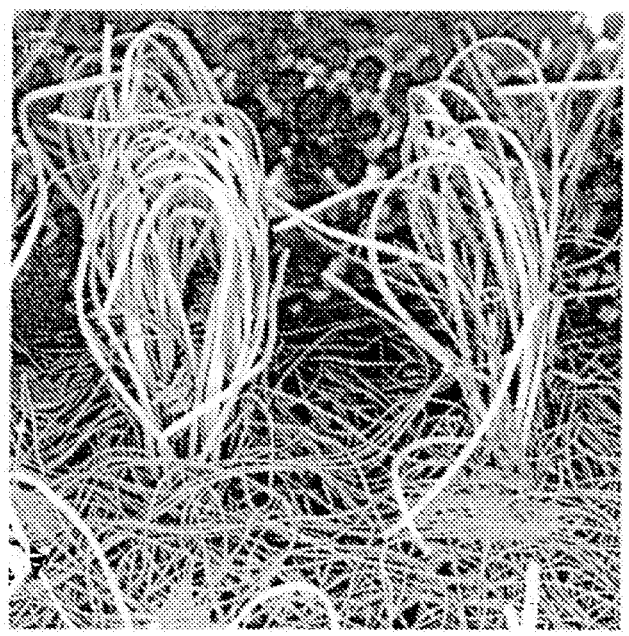

FIG. 15 is a photomicrograph of Sample 4, which comprises three precursor webs. The first and third precursor webs of Sample 4 were a spunbond polypropylene nonwoven having a basis weight of 13.5 gsm, designated NW30 from First Quality Nonwovens, Haxleton, Pa. The first and third precursor webs were the outer layers, sandwiching the second precursor web which was a loosely bonded airlaid nonwoven web made from 44 mm (1.75 inch) long staple fibers comprising polyester fibers and PE/PP 50/50 core/sheath nonwoven bicomponent binder fibers in an 80/20 fiber ratio by weight, respectively. The polyester fibers were Type 1311 fibers and the PE/PP fibers were Type 851607 fibers, both fibers being available from FIT (Fiber Innovation Technology) Inc., Johnson City, Tenn. Sample 4 was produced on an apparatus as described above with respect to FIG. 5 at a line speed of approximately 30 meters per minute (100 feet per minute). As shown in FIG. 15, in some embodiments of web 1 there may be no flaps 7 to speak of, but only a slight disruption of second precursor web around the opening through which tufts 6 extend. The tufts 6 shown in FIG. 15 can be seen to comprise two fiber types. Fibers from both the middle, sandwiched airlaid web, and one of the outer layers contribute to the tuft 6.

As can be understood from the above description of webs 1 and apparatus 100 of the present invention, many various structures of webs 1 can be made without departing from the scope of the present invention as claimed in the appended claims. For example, webs 1 can be coated or treated with lotions, medicaments, cleaning fluids, anti-bacterial solutions, emulsions, fragrances, surfactants. Likewise, apparatus 100 can be configured to only form tufts 6 on a portion of the web 1, or to form varying sizes or area densities of tufts 6.

Another advantage of the process described to produce the webs of the present invention is that the webs can be produced in-line with other web production equipment or in-line with disposable absorbent article production equipment. Additionally, there may be other solid state formation processes that can be used either prior to or after the process of the present invention. For example, a web could be processed according to the present invention and then apertured with a stretching process, such as one described in U.S. Pat. No. 5,658,639 to Curro et al. Alternatively, a material could be made into a composite through a variety of processes, such as one described in US Publication No. 2003/028,165A1 to Curro et al. or ring rolled, for example as in U.S. Pat. No. 5,167,897 to Weber et al. and then processed according to the present invention. The resulting webs can thus exhibit the combined benefits of these multiple material modifications.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A laminate web comprising first and second precursor webs, said laminate web having a machine direction and a cross machine direction defining a MD-CD plane, at least the first precursor web being a nonwoven web, the laminate web having a first side, the first side comprising the second precursor web and at least one discrete tuft, each of the discrete tufts having a linear orientation defining a longitudinal axis in said MD-CD plane and comprising a plurality of tufted fibers being integral extensions of the first precursor web and extending through the second precursor web; and a second side, the second side comprising the first precursor web; wherein said plurality of tufted fibers being integral extensions of the first precursor web comprises both a first plurality of looped fibers and a second plurality of non-looped fibers, and wherein said first plurality of looped fibers define a tunnel-like shaped tuft having opposing longitudinal open ends.

2. The laminate web of claim 1, wherein said web comprises a plurality of discrete tufts.

3. The laminate web of claim 1, wherein said first precursor web comprises a nonwoven web of substantially randomly oriented fibers.

4. The laminate web of claim 1, wherein a portion of each said tuft defines an open void area internal to said tufts.

5. A wipe comprising said laminate web of claim 1.

6. A disposable absorbent article, said article having at least one component comprising a laminate web, said laminate web having a machine direction and a cross machine direction defining a MD-CD plane, said laminate web comprising first and second precursor webs, at least the first precursor web being a nonwoven web, the laminate web having a first side, the first side comprising the second precursor web and at least one discrete tuft, each of the discrete tufts having a linear orientation defining a longitudinal axis in said MD-CD plane and comprising a plurality of tufted fibers being integral extensions of the first precursor web and extending through the second precursor web; and a second side, the second side comprising the first precursor web; wherein said plurality of tufted fibers being integral extensions of the first precursor web comprises both a first plurality of looped fibers and a second plurality of non-looped fibers, and wherein said first plurality of looped fibers define a tunnel-like shaped tuft having opposing longitudinal open ends.

7. The article of claim 6, wherein said article is selected from the group consisting of a catamenial device, a tampon, or a diaper.

8. The article of claim 6 wherein said laminate web comprises a topsheet of said disposable absorbent article.

9. The article of claim 6 wherein said laminate web comprises a core of said disposable absorbent article.

10. The laminate web of claim 1, wherein at least one of said first precursor web and said second precursor web comprises nanofibers having a mean diameter of less than 1 micron.

11. The article of claim 6, wherein at least one of said first precursor web and said second precursor web comprises nanofibers having a mean diameter of less than 1 micron.

12. A laminate web comprising first and second precursor webs, said laminate web having a machine direction and a cross machine direction defining a MD-CD plane, at least the first precursor web being a nonwoven web, the laminate web having a first side, the first side comprising the second precursor web and at least one discrete tuft, each of the discrete tufts having a linear orientation defining a longitudinal axis in said MD-CD plane and comprising a plurality of tufted fibers being integral extensions of the first precursor web and extending through the second precursor web; and a second side, the second side comprising the first precursor web; wherein said plurality of tufted fibers comprises looped fibers that collectively define a tunnel-like shaped tuft having opposing longitudinal open ends.

* * * * *